(12) United States Patent
Melmed et al.

(10) Patent No.: US 6,909,030 B2
(45) Date of Patent: Jun. 21, 2005

(54) PTTG KNOCKOUT RODENT AS A MODEL TO STUDY MECHANISMS FOR VARIOUS PHYSIOLOGICAL PHENOMENA, INCLUDING DIABETES

(75) Inventors: Shlomo Melmed, Los Angeles, CA (US); Zhiyong Wang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 58 days.

(21) Appl. No.: 09/978,146

(22) Filed: Oct. 15, 2001

(65) Prior Publication Data

US 2003/0106080 A1 Jun. 5, 2003

(51) Int. Cl.$^7$ ........................ G01N 33/00; A01K 67/00; A01K 67/027

(52) U.S. Cl. ............................ 800/3; 800/13; 800/14; 800/18

(58) Field of Search ........................... 800/3, 13, 14, 800/18, 9

(56) References Cited

U.S. PATENT DOCUMENTS

| | | | |
|---|---|---|---|
| 5,684,222 A | 11/1997 | Mak | 800/2 |
| 5,714,667 A | 2/1998 | Waterhouse et al. | 800/2 |
| 5,814,300 A | 9/1998 | Scott et al. | 424/911 |
| 5,844,107 A | 12/1998 | Hanson et al. | 536/23.1 |
| 5,877,302 A | 3/1999 | Hanson et al. | 536/23.1 |
| 5,972,900 A | 10/1999 | Ferkol, Jr. et al. | 514/44 |
| 5,972,901 A | 10/1999 | Ferkol, Jr. et al. | 514/44 |
| 6,077,835 A | 6/2000 | Hanson et al. | 514/44 |
| 6,087,555 A | 7/2000 | Dunstan et al. | 800/18 |
| 6,136,040 A | 10/2000 | Ornitz et al. | 8/18 |

FOREIGN PATENT DOCUMENTS

| | | |
|---|---|---|
| JP | 7322892 A2 | 12/1995 |
| JP | 9173053 A2 | 7/1997 |
| WO | WO 90/09442 | 8/1990 |
| WO | WO 95/25809 | 9/1995 |
| WO | WO 98/22587 | 5/1998 |
| WO | WO 98/39412 | 9/1998 |

OTHER PUBLICATIONS

Wu et al., Methods in Gene Biotechnology, 1997, CRC Press, Boca Raton, p. 339–365.*
Houdebine, Louis–Marie, 1994, Journal of Biotechnology, vol. 34, p. 269–287.*
Sigmund, C., 2000, Arterioscler Thromb Vasc Biol., vol. 20, p. 1425–1429.*
Seamark, R. F., 1994, Reprod. Fertil. Dev., vol. 6, p. 653–657.*
Wolfer et al., 2002, Trends in Neurosciences, vol. 25, No. 7, p. 336–340.*
Marra, M., et al., "The WashU–HHMI Mouse EST project, AC W81747", EMBL Database, Jun. 27, 1996, Heidelberg, XP002066845.
Hillier, L., et al., The WashU–Merck EST project, AC AA007646, EMBL Database, Jul. 28, 1996, Heidelberg, XP002066846.
Holton, T., et al., "ACQ57612", EMBL Database, Sep. 5, 1994, Heidelberg, XP002066847.
Nippon Telegraph and Telephone Corp.: "ACQ75553", EMBL Database, Aug. 4, 1995, Heidelberg, XP002066848.
Gonsky, R., et al., "Transforming DNA Sequences Present in Human Prolactin–Secreting Pituitary Tumors", Molec. Endocrin., 5(11): 1687–1695, Nov. 1991.
Pei, L., et al., "Isolation and Characterization of a Pituitary Tumor–Transforming Gene (PTTG)", Molec. Endocrin., 11(4): 433–441, Apr. 1997.
Shimon, I., et al., "Genetic Basis of Endocrine Disease", J. Clin. Endocrin. And Metab., 82(6): 1675–1681, Jun. 1997.
Chen, L., et al., "Identification of the human pituitary tumor transforming gene (hPTTG) family: molecular structure, expression, and chromosomal localization.", 1: Gene 2000, May 2; 248 (102): 41–50.
Heaney, A.P., "Expression of pituitary–tumor transforming gene in colorectal tumours", 1: Lancet 2000 Feb. 26; 355(9205):716–9.
Heaney, A.P., "Early Involvement of Estrogen–induced pituitary tumor transforming gene and fibroblast growth factor expression in prolactinoma pathogenesis", 1: Nat Med 1999, Nov; 5(11): 1317–21.
Suhardja, A.S., et al., "Molecular pathogenesis of pituitary adenomas: a review.", Acta Neurochir (Wien) 1999; 141(7): 729–36. Abstract Only.
Ren, R., et al., "Identification of a ten–amino acid proline–rich SH3 binding site.", Science 1993 Feb 19; 259(5098): 1157–61. Abstract Only.

(Continued)

Primary Examiner—Shin-Lin Chen
(74) Attorney, Agent, or Firm—Seth D. Levy; Davis Wright Tremaine LLP

(57) ABSTRACT

Disclosed is a null mutant (or knockout) rodent comprising in its germ cells an artificially induced PTTG null mutation. In some embodiments, the null mutant rodent can be generated by way of homologous recombination in an embryonic stem cell or germ cell. The inventive null mutant rodent can be used to study mammalian physiology at the cellular, tissue, and/or organismal level with respect to various phenotypes, including hyperglycemia, hypoinsulinaemia, hypoleptinemia, diabetes, chromosomal aneuploidy, premature centromere division, chromosomal damage, aberrant mitotic cellular division, thrombocytopenia, thymic hyperplasia, splenic hypoplasia, testicular hypoplasia, and female subfertility. Also disclosed is an animal model for diabetes. Also disclosed is a somatic or germ cell obtained from the null mutant rodent. Also disclosed is a cell line derived from a cell obtained from the null mutant rodent.

18 Claims, 7 Drawing Sheets

OTHER PUBLICATIONS

Liu, X., et al., "The v–Src SH3 domain binds phosphatidylinositol 3'–kinase.", Mol Cell Biol 1993 Sep; 13(9): 5225–32. Abstract Only.

Gout, I., et al., "The GTPase dynamin binds to and is activated by a subset of SH3 domains." Cel 1993 Oct 8; 75(1): 25–36.

Yu, H., et al., "Solution structure of the SH3 domain of Src and identification of its ligan–binding site." Science 1992 Dec 4; 258(5088): 1665–8. Abstract Only.

Lee, I.A., et al., "Cloning and expression of human cDNA encoding human homologue of pituitary tumor transforming gene.", Biochem Mol. Biol Int 1999 May; 47(5): 891–7. Abstract Only.

Zou, H., et al., "Identification of a vertebrate sister–chromatid separation inhibitor involved in transformation and tumorigenesis.", Science 1999 Jul 16; 285(5426): 418–22. Abstract Only.

Zhang, X., et al., "Pituitary tumor transforming gene (PTTG) expression in pituitary adenomas." J Clin Endocrinol Metab 1999 Feb; 84(2): 761–7.

Prezant, T.R., et al., "An intronless homolog of human proto–oncogene hPTTG is expressed in pituitary tumors; evidence fo hPTTG family.", J Clin Endocrinol Metab 1999 Mar; 84(3): 1149–52.

Fujimoto, N., et al., "Establishment of an estrogen responsive rat pituitary cell sub–line MtTE–2." Endocr J 1999 Jun.; 46(3): 389–96. Abstract Only.

Ramos–Morales, F., et al., "Cell cycle regulated expression and phosphorylation of hpttg proto–oncogene product.", Oncogene 2000 Jan 20; 19(3): 403–9. Abstract Only.

McCabe C.J., et al., "PTTG—a new pituitary tumour transforming gene.", J Endocrinol 1999 Aug; 162(2): 163–6.

Kakar, S.S., "Molecular cloning, genomic organization, and identification of the promoter for the human pituitary tumor transforming gene (PTTG).", Gene 1999 Nov 29; 240(2): 317–24. Abstract Only.

Dominguez, A., et al., "hpttg, a human homologue of rat pttg, is overexpressed in hematopoietic neoplasms. Evidence for a transcriptional activation function of hPTTG.", Oncogene 1998 Oct 29; 17(17): 2187–93. Abstract Only.

Pei, L., "Pituitary tumor–transforming gene protein associates with ribosomal protein S10 and a novel human homologue of DnaJ in testicular cells.", J Biol Chem 1999 Jan 29; 274(5): 3151–8.

Saez, C., et al., "hpttg is over–expressed in pituitary adenomas and other primary epithelial neoplasias.", Oncogene 1999 Sep 23; 18(39): 5473–6. Abstract Only.

Pei, L., "Genomic Organization and identification of an enhancer element containing binding sites for multiple proteins in rat pituitary tumor–transforming gene.", J Biol Chem 1998 Feb 27; 273(9): 5219–25.

Wang, Z., et al., "Characterization of the murine pituitary tumor transforming gene (PTTG) and its promoter.", Endocrinology 2000 Feb; 141(2): 763–71.

Zhang, X., et al., "Structure, expression, and function of human pituitary tumor–transforming gene (PTTG).", Mol Endocrinol 1999 Jan; 13(1): 156–66.

Heaney, Anthony, P., et al., "Pituitary tumor transforming gene: a novel factor in pituitary tumour formation," Balliere's Clinical Endocrinology and Metabolism, vol. 13, No. 3, pp. 367–380, 1999.

Krieger, N.R., et al., *Rat pancreatic islet and skin xenograft survival in CD4 and CD8 knockout mice, J. Autoimmun.,* 10(3):309–15 (Jun 1997). Abstract Only.

Wang, Z., et al., *Pituitary tumor transforming gene (PTTG) transforming and transactivation activity, J. Biol. Chem.,* 275(11):7459–61 (Mar 17, 2000).

Dubik, D., et al., *Mechanism of estrogen activation of c–myc oncogene expression, Oncogene,* 7(8):1587–94 (Aug 1992). Abstract Only.

Farrell, W.E., *Molecular Pathogenesis of Pituitary Tumors, Front Neuroendocrinol.,* 21(3):174–198 (Jul 2000). Abstract Only.

Pei, L., *Activation of mitogen–activated kinase cascade regulates pituitary tumor–transforming gene transactivation function, J. Biol. Chem.* 275(40):31191–8 (Oct 6, 2000). Abstract Only.

Shepel, L.A., et al., *Relationship of polymorphisms near the rat prolactin, N–ras, and retinoblastoma genes with susceptibility to estrogen–induced pituitary tumors, Cancer Res.,* 50 (24):7920–5 (Dec 15, 1990). Abstract Only.

Sutherland, R.L, et al., *Estrogen and progestin regulation of cell cycle progression, J. Mammary Gland Biol. Neoplasia* 3(1):63–72 (Jan, 1998). Abstract Only.

Yu, R., et al., *Pituitary–tumour transforming gene (PTTG) regulates placental JEG–3 cell divisio and survival: evidence from live cell imaging, Mol. Endocrinol.* 14(8):1137–46 (Aug. 2000). Abstract Only.

Zou, H. et al., *Identification of a vertebrate sister–chromatid separation inhibitor involved in transformation and tumorigenesis, Science* 285(5426):418–22 (Jul. 16, 1999). Abstract Only.

Tarabykin, V., et al., *Expression of PTTG and prcl during telencephalic neurogenesis, Mech. Dev.* 92(2):301–04 (Apr. 2000). Abstract Only.

Mei, J., et al., *Securin is not required for cellular viability, but is required for normal growth of mouse embryonic fibroblasts, Current Biology* 11:1197–1201 (2001).

* cited by examiner a -/- b -/-

PTTG KNOCKOUT RODENT AS A MODEL TO STUDY MECHANISMS FOR VARIOUS PHYSIOLOGICAL PHENOMENA, INCLUDING DIABETES

BACKGROUND OF THE INVENTION

Throughout the application, various publications are referenced in parentheses. The disclosures of these publications in their entireties are hereby incorporated by reference in the application in order to more fully describe the state of the art to which this invention pertains.

1. Field of the Invention

The present invention is related to the biomedical arts, in particular to genetics.

2. Discussion of the Related Art

The particular gene that is the subject of the present invention is PTTG, which is believed to have a role in proper cell cycle progression.

Events such as DNA synthesis, chromosome segregation, spindle assembly, cytokinesis, and other aspects of cell division, must be executed in ordered sequence during the cell cycle. Proper cell cycle progression is a complex process requiring many cell cycle regulators including p53, Rb, cyclins, cdks and cdk inhibitors p21, and p16, among others. (Reddel, R. R., *Genes involved in the control of cellular proliferative potential*, Ann. N.Y. Acad. Sci. 854: 8–19 [1998]; Prosperi, E., *Multiple roles of the proliferating cell nuclear antigen: DNA replication, repair and cell cycle control*, Prog. Cell Cycle Res. 3:193–210 [1997]). Loss or mutation of these genes leads to dysfunctions of cell cycle progression and are frequently involved in tumorigenesis and apoptosis resulting in pathological consequences. For example, mice lacking p53 show unregulated G1 checkpoint control and a high prevalence of spontaneous tumor development (Donehower, L. A., et al., *Mice deficient for p53 are developmentally normal but susceptible to spontaneous tumors*, Nature 356:215–221 [1992]); mice lacking Rb do not survive fetal development while Rb+/− mice developed pituitary tumors at 8 months (Jacks, T., et al., *Effects of an Rb mutation in the mouse*, Nature 359:295–300 [1992]); mice lacking p21 undergo normal development but show defective G1 checkpoint control (Deng, C., et al., *Mice lacking p21CIP1WAFI undergo normal development, but are defective in G1 checkpoint control*, Cell 82:675–684 [1995]).

Recently, a family of proteins including securins, separins and cohesins were found to play important roles during sister chromatid separation in eukaryotic cell cycle M phase (Nasmyth, K., et al., *Splitting the chromosome: cutting the ties that bind sister chromatids*, Science 288:1379–1384 [2000]). These proteins exhibit characteristics of cell cycle regulators. Securins (e.g., *S. cerevisine* Pds1p, *S. prombe* Cut2, *Drosophila* PIM, *Xenopus* securin) share at least one destruction box and a nine amino acid consensus motif [RX(A or V or L) LGXXX N], originally identified in B-type cyclins. (Ciosk, R., et al., *An ESP1/PDS1 complex regulates loss of sister chromatid cohesion at the metaphase to anaphase transition in yeast*, Cell 93:1067–1076 [1998]; Funabiki, H., et al., *Fission yeast Cut1 and Cut2 are essential for sister chromatid separation, concentrate along the metaphase spindle and form large complexes*, Embo. J. 15:6617–6628 [1996]; Zou, H., et al., *Identification of a vertebrate sister-chromatid separation inhibitor involved in transformation and tumorigenesis*, Science 285:418–422 [1999]; Stratmann, R., et al., *Separation of sister chromatids in mitosis requires the Drosophila pimples product, a protein degraded after the metaphase/anaphase transition*, Cell 84: 25–35 [1996]). The separins (Esp1p, Cut1, BimB) share a conserved carboxy-terminal domain, which binds to securins (Ciosk, R., et al., *An ESP1/PDS1 complex regulates loss of sister chromatid cohesion at the metaphase to anaphase transition in yeast*, Cell 93:1067–1076 [1998]; Funabiki, H., et al., *Fission yeast Cut1 and Cut2 are essential for sister chromatid separation, concentrate along the metaphase spindle and form large complexes*, Embo. J. 15:6617–6628 [1996]; May, G. S., et al., *The bimB3 mutation of Aspergillus nidulans uncouples DNA replication from the completion of mitosis*, J. Biol. Chem. 267:15737–15743 [1992]).

Securins reach their highest expression level in M phase. Securins accumulate during interphase, and they bind to separin, which prevents premature separin activation. In a normal cell cycle, anaphase promoting complex (APC) eventually degrades securins, thus activating separin to facilitate chromosome segregation. (Nasmyth, K., et al., *Splitting the chromosome: cutting the ties that bind sister chromatids*, Science 288:1379–1384 [2000]). In this sense, securins function as inhibitors of chromatid separation during anaphase.

To date, characterization of mammalian securin or separin has been limited. (Zou, H., et al., *Identification of a vertebrate sister-chromatid separation inhibitor involved in transformation and tumorigenesis*, Science 285:418–422 [1999]).

However, pituitary tumor transforming gene (PTTG) (Pei, L., et al., *Isolation and characterization of a pituitary tumor-transforming gene (PTTG)*, Mol. Endo. 11:433–441 [1997]), a recently described oncogene isolated from pituitary tumor growth hormone-secreting cells by differential display, has 44.6% amino acid identity with *Xenopus* securin. Indeed, PTTG has one destruction box (RXLGXXXN) and cyclin B-like 9 amino acid consensus motif. PTTG protein preferentially localizes in the cell nucleus. (Yu, R., et al., *Pituitary tumor transforming gene (PTTG) regulates placental JEG-3 cell division and survival: evidence from live cell imaging*, Mol. Endo. 14:1137–1146 [2000]). Expression levels of PTTG protein change in a temporal pattern during cell cycle progression, peaking during M phase; PTTG is phosphorylated by cdc2 and MAPK. (Ramos-Morales, F., et al., *Cell cycle regulated expression and phosphorylation of hpttg proto-oncogene product*, Oncogene 19:403–409 [2000]; Pei, L., *Activation of mitogen-activated protein kinase cascade regulates pituitary tumor transforming gene transactivation function*, J. Biol. Chem. 275:31191–31198 [2000]). PTTGs have been identified in rat, mouse, and human cells. (e.g., PCT/US97/21463; Wang, Z., et al., *Pituitary tumor transforming gene (PTTG) transforming and transactivation activity*, J. Biol. Chem. 275:7459–7461 [2000]).

PTTG1, the PTTG equivalent in humans, is expressed at low levels in most normal human tissues. (Chen, L. et al., *Identification of the human pituitary tumor transforming gene (hPTTG) family: molecular structure, expression, and chromosomal localization*, Gene. 248:41–50 [2000]; Heaney, A. P. et al. [2000]). PTTG is abundant only in normal testis and thymus. (Wang, Z., et al., *Characterization of the murine pituitary tumor transforming gene (PTTG) and its promoter*, Endocrinology 141:763–771 [2000]). When expressed at normal levels, PTTG mediates promoter transcriptional activation. (Wang, Z., et al., *Pituitary tumor transforming gene (PTTG) transforming and transactivation activity*, J. Biol. Chem. 275:7459–7461 [2000]), utilizes c-myc as its downstream gene target. By dysregulating chromatid separation, PTTG overexpression also leads to aneuploidy, i.e., cells having one or a few chromosomes above or below the normal chromosome number (Zou et al. [1999]; Yu, R. et al. [2000]). At the end of metaphase, securin is degraded by an anaphase-promoting complex, releasing tonic inhibition of separin, which in turn mediates degradation of cohesins, the proteins that hold sister chromatids together. Overexpression of a nondegradable PTTG disrupts sister chromatid separation (Zou et al. [1999]) and overexpression of PTTG causes apoptosis and inhibits mitoses (Yu, R. et al. [2000]). The securin function of PTTG suggests that PTTG may also be expressed in normal proliferating cells. In adult humans, PTTG1 mRNA is most abundant in testis, an organ containing rapidly proliferating gametes. (Zhang, X. et al. [1999a]); Wang, Z. et al. [2000]).

In contrast, PTTG1 is highly expressed in human tumors and is responsive to estrogen induction. (Zhang, X., et al., *Structure, expression, and function of human pituitary tumor-transforming gene (PTTG)*, Mol. Endo. 13:156–166 [1999]; Heaney, A. P., et al., *Early involvement of estrogen-induced pituitary tumor transforming gene and fibroblast growth factor expression in prolactinoma pathogenesis*, Nature Med. 5:1317–1321 [1999]). Indeed, PTTG is highly expressed in pituitary tumors and neoplasms from the hematopoietic system and colon, and PTTG is considered to be a proto-oncogene, because PTTG overexpression in NIH3T3 cells induces cell transformation and in vivo tumor formation. (Pei, L., et al., *Isolation and characterization of a pituitary tumor-transforming gene (PTTG)*, Mol. Endo. 11:433–441 [1997]; Zhang, X. et al., *Structure, expression, and function of human pituitary tumor-transforming gene (PTTG)*, Mol. Endocrinol. 13:156–66 [1999a]; Zhang, X. et al., *Pituitary tumor transforming gene (PTTG) expression in pituitary adenomas*, J. Clin. Endocrinol. Metab. 84:761–67 [1999b]; Heaney, A. P. et al., *Pituitary tumor transforming gene in colorectal tumors*, Lancet 355:712–15 [2000]; Dominguez, A. et al., *hPTTG, a human homologue of rat pttg, is overexpressed in hematopoietic neoplasms. Evidence for a transcriptional activation function of hPTTG*, Oncogene 17:2187–93 [1998]; Saez, C. et al., *hPTTG is overexpressed in pituitary adenomas and other primary epithelial neoplasias*, Oncogene 18:5473–6 [1999]). In addition, PTTG has been shown to possess other physiological roles in mammals, although mechanisms are unclear.

PTTG also has been shown to upregulate basic fibroblast growth factor secretion (Zhang, X. et al. [1999a]), and transactivate DNA transcription (Dominguez, A. et al. [1998]; Wang, Z. et al., *Pituitary tumor transforming gene (PTTG) transactivating and transforming activity*, J. Biol. Chem. 275:7459–61[2000]).

The recent discovery of human PTTG2 gene, which shares high sequence homology with human PTTG1, implies the existence of a PTTG family. (Prezant, T. R., et al., *An intronless homolog of human proto-oncogene hPTTG is expressed in pituitary tumors: evidence for hPTTG family*, J. Clin. Endocrinol. Metab. 84:1149–1152 [1999]). There is evidence that a PTTG family consists of at least three genes that share a high degree of sequence homology, including human PTTG1, located on chromosome 5q33. (Id.). Murine PTTG shares 66% nucleotide base sequence homology with human PTTG1 and also exhibits transforming ability. (Wang, Z. and Melmed, S., *Characterization of the murine pituitary tumor transforming gene (PTTG) and its promoter*, Endocrinology 14:763–771 [2000].

Despite all of the research and resources applied to understanding the role of PTTG in cell cycle control and the pathogenesis of numerous disease conditions, including tumorigenesis, the function and mode of action of PTTG in vivo remains poorly understood. This is due, in part, to the fact that there has been no readily available and effective in vivo model for studying PTTG.

In a recently published article, researchers claim to have obtained three "securin-null" mice of both sexes. (Mei, J., Huang, X., and Zhang, P., *Securin is not required for cellular viability, but is required for normal growth of mouse embryonic fibroblasts*, Current Biology 11:1197–1201 [2001]). The securin referred to is represented to be PTTG. Aside from the observation that PTTG –/– MEFs exhibited delayed cell cycle progression of G2-M phase, no other phenotypic differences from wild-type were observed in either the PTTG –/– mice or the cells derived therefrom.

There remains a need for an in vivo model for studying the role of PTTG in mammalian physiology at the cellular, tissue, and/or organismal level, including the study of diabetes, cell cycle control, oncogenesis, and various other medical conditions and phenomena relating to PTTG expression. This and other benefits are provided by the present invention as described herein.

SUMMARY OF THE INVENTION

The present invention, which addresses the above-described needs, provides a rodent, such as a mouse or rat, having an artificially induced PTTG null mutation in its germ line cells. In some embodiments, functional PTTG protein is not expressed in somatic cells of the null mutant rodent. Useful somatic and germ cells and cell lines obtained from the PTTG null mutant rodent also are provided by the present invention.

The present invention also relates to uses for the PTTG null mutant rodent in the study of mammalian physiology at the cellular, tissue, and/or organismal level. In some embodiments, the null mutant rodents of the present invention exhibit numerous phenotypic differences over their wild-type counterparts, including diabetes, hyperglycemia, hypoinsulinaemia, hypoleptinemia, chromosomal aneuploidy, premature centromere division, chromosomal damage, aberrant mitotic cellular division, thrombocytopenia, thymic hyperplasia, splenic hypoplasia, testicular hypoplasia, and female subfertility.

Hyperglycemia and hypoinsulinaemia are important features of diabetes. Established animal models for diabetes with hyperglycemia and hypoinsulinaemia include NOD (non-obese-diabetes) mice and STZ (streptozotocin)-treated mice. NOD mice are known to have a polygenic susceptibility to diabetes, while STZ is a synthetic chemical compound harmful to the pancreas. Elucidation of underlying mechanisms for diabetes development has been complicated due to the variables inherent in these two models. In contrast, PTTG knockout mice were generated from a single gene disruption; PTTG involvement in the insulin action, thus, should be less complicated to decipher than that of multiple genetic factors in NOD or unknown factors in the STZ model. The present invention allows for more effective screening for drug candidates for treating diabetes.

BRIEF DESCRIPTION OF THE FIGURES

FIG. 1A shows the genomic structure of the murine PTTG gene and a schematic diagram of the targeting vector. Endogenous PTTG contains five exons, depicted as E1–E5. A 4.2 kb Hind III—EcoR I fragment of PTTG including exons 2, 3 and part of exon 1 was replaced with a pGK-neo cassette. The filled box designated "probe" represents the region used for Southern blotting. FIG. 1B illustrates the results of a Southern blot analysis of genomic DNA derived from mouse tails with the indicated PTTG genotype. DNA was digested with Hind III and probed with the labeled 350 bp fragment shown in FIG. 1A. FIG. 1C sets forth the results of Northern blot analysis of total RNA derived from mouse testis with the indicated PTTG genotype. Murine PTTG exon 3 cDNA fragment was used as probe.

FIG. 3A is an insulin immunostaining comparison in a PTTG +/+ and PTTG −/− pancreas. Paraffin-embedded pancreatic sections (5 μm) were processed as instructed in the kit manual (LSAB2 system, HRP; DAKo Corporations, Carpinteria, Calif.), wherein anti-insulin antibody was used as the first antibody. Cells showing up in dark shade in this figure represent insulin-secreting cells. Panel 1 depicts an insulin immunostained PTTG +/+ pancreas; Panel 2 depicts an insulin immunostained PTTG −/− pancreas; and Panel 3 depicts an insulin immunostained PTTG −/− pancreas. FIG. 3B depicts Hematoxylin and Eosin staining of PTTG +/+ and PTTG −/− mouse pancreases. Paraffin-embedded pancreatic sections were processed according to standard protocol as described in Brown, Geoffrey G. An introduction to histotechnology: a manual for the student, practicing technologist, and resident-in-pathology/, Geoffrey G. Brown: foreword by John M. Budinger. New York: Appleton-Century-Crofts, [c1978]. Note the high percentage occupance of lymphocytes (the darkly shaded dots) in islets in Panels 2 and 3 rather than 1. Panel 1 depicts a stained PTTG +/+ pancreas; Panel 2 a PTTG −/− pancreas; and Panel 3 a PTTG −/− pancreas.

FIG. 4A shows photographs of testis (30 weeks), spleen (5 weeks) and thymus (5 weeks) from PTTG +/+ and PTTG −/− mice. In FIG. 4B, the relative distribution of thymocyte subsets in the 5-week thymus were determined by staining for expression of indicated lineage-specific cell surface antigens and cell sorting by flow cytometry. Relative percentages of cells exhibiting each cell surface characteristic are indicated. FIG. 4C depicts tail bleeding times for PTTG +/+ and PTTG −/− mice at 8 weeks. Each point represents one individual mouse, and results were generated from two separate experiments in 12 mice.

FIG. 5B shows the results of flow cytometry analysis of PTTG +/+ and PTTG −/− MEFs. MEFs were plated 18 hrs before treatment (timepoint 0) and collected at the indicated timepoints for flow cytometry analysis. Treatments included: 1. control without treatment; 2. 12-Gy γ-irradiation; 3. transfection of PTTG retrovirus; 4. serum starvation (with 0.1% FBS).

FIG. 6A depicts binucleated and multinucleated cells in PTTG −/− MEFs. At least 1000 cells were counted. FIG. 6B illustrates aberrant chromosomal morphology in PTTG −/− MEF metaphase spreads. Three different fields are depicted, in which quadriradial, triradial and chromosome breaks are present as arrowed. Aneuploidy is also apparent in these metaphases.

DETAILED DESCRIPTION OF THE PREFERRED EMBODIMENTS

Figure 1:
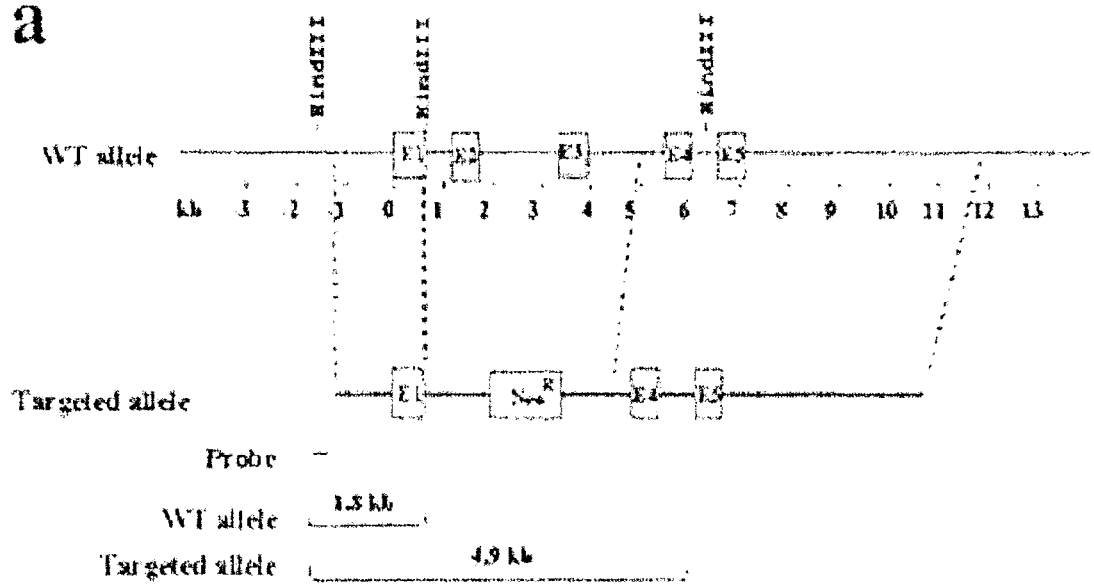
FIG. 1 depicts a schematic diagram of the targeting strategy for mutation of the PTTG gene.
Figure 1:
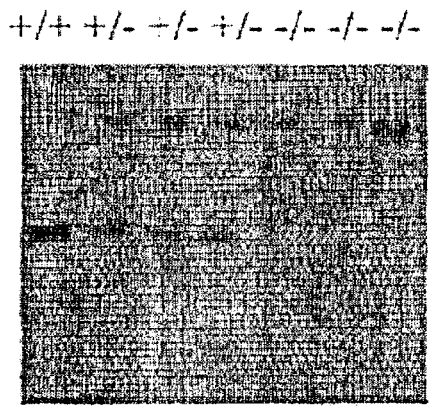
Figure 1:
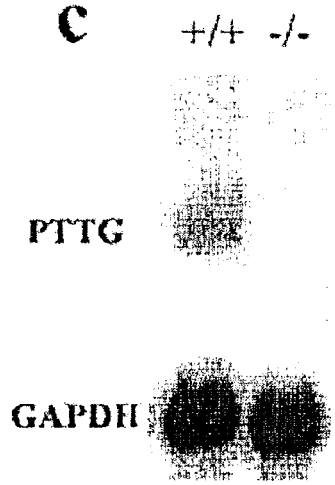

The present invention relates to a rodent comprising in its germ cells an artificially induced PTTG null mutation.

The terms "rodent" and "rodents" refer to all members of the phylogenetic order Rodentia (e.g., mice, rats, squirrels, beavers, woodchucks, gophers, voles, marmots, hamsters, guinea pigs, and agoutas) including any and all progeny of all future generations derived therefrom. The term "murine" refers to any and all members of the family Muridae, including without limitation, rats and mice.

In accordance with the present invention, the null mutation is artificially induced. Artificial induction of a mutation is accomplished by any means now known or later developed. This includes known techniques such as homologous recombination, transpositional recombination, site directed mutation, and artificial induction of frame shift mutations.

As used herein, the term "null mutation" refers to a mutation in both genomic copies of an endogenous gene (such as PTTG) of an embryonic stem cell or mammal, such that the translation products, which is/are typically expressed in cells bearing the wild-type genotype, are not expressed or are not functional in at least one aspect in cells of the targeted organism. The rodent can be a "heterozygous null", wherein one allele of the endogenous gene has been mutated. Alternatively, the rodent can be a "homozygous null" wherein both alleles of the endogenous gene have been mutated.

The term "functional," when used herein as a modifier of PTTG protein(s), peptide(s), or fragments thereof, refers to a polypeptide that exhibits at least one of the functional characteristics or biological activities attributed to PTTG. For example, one biological activity of PTTG is the ability to transform cells in vitro (e.g., NIH 3T3 and the like). Another biological activity is the ability to modulate the activation of mammalian T-lymphocytes. Another biological activity of PTTG is the ability to inhibit separin activity in the nucleus during mitosis. Yet another biological activity of PTTG is the ability to induce neoplastic cellular proliferation (e.g., tumorigenesis) in nude mice (e.g., when transfected into NIH 3T3 cells and the like). Another biological activity is the ability to act as an antigen to stimulate in a mammal the production of specific anti-PTTG antibodies, or the ability to bind to specific anti-PTTG antibodies.

As used herein, the term "mating" means copulation by the male and female rodents of the same species, or breeding by in vitro or in vivo artificial means to obtain further generations of progeny. Artificial means include, but are not limited to, artificial insemination, in vitro fertilization (IVF) and/or other artificial reproductive technologies, such as intracytoplasmic sperm injection (ICSI), subzonal insemination (SUZI), or partial zona dissection (PZD). However, others, such as cloning and embryo transfer, cloning and embryo splitting, and the like, can also be employed.

A "transgenic" or "recombinant" rodent is one that has had foreign or exogenous DNA introduced into its germ line cells. The exogenous genes which have been introduced into the animal's cells are called "transgenes" or "recombinants." The transfected germ cells of the transgenic vertebrate animal preferably have the non-endogenous (exogenous) genetic material (such as a targeting vector) integrated into their chromosomes. Those skilled in the art will readily appreciate that any desired traits generated as a result of changes to the genetic material of any transgenic vertebrate produced by this invention are heritable. Although the genetic material was originally inserted solely into the germ cells of a parent animal, it will ultimately be present in the germ cells of direct progeny and subsequent generations of offspring. The genetic material is also present in the differentiated cells, i.e. somatic cells, of the progeny.

A "targeting vector" is a polynucleotide sequence that is designed to suppress or, preferably, eliminate expression or function of a polypeptide encoded by an endogenous gene in one or more cells of a mammal. The polynucleotide sequence used as the targeting vector is typically comprised of (1) DNA from some portion of the endogenous gene (one or more exon sequences, intron sequences, and/or promoter sequences) to be suppressed and (2) a selectable marker sequence used to detect the presence of the targeting vector in a cell. The targeting vector is inserted into a cell containing the endogenous gene to be artificially mutated. The targeting vector can then integrate within one or both alleles of the endogenous PTTG gene, and such integration of the PTTG targeting vector can prevent or interrupt transcription of the full-length endogenous PTTG gene. Integration of the PTTG targeting vector into the cellular chromosomal DNA is typically accomplished via homologous recombination (i.e., regions of the PTTG targeting vector that are homologous or complimentary to endogenous PTTG DNA sequences can hybridize to each other when the targeting vector is inserted into the cell; these regions can then recombine so that the targeting vector is incorporated into the corresponding position of the endogenous DNA).

A "selectable marker sequence" is a polynucleotide sequence, the incorporation of which into the chromosome of a cell, is capable of detection. That is, it is a polynucleotide sequence that is (1) used as part of a larger nucleotide sequence construct (i.e., the "targeting vector") to disrupt the expression of PTTG, and (2) used as a means to identify those cells that have incorporated the PTTG targeting vector into the chromosomal DNA. The selectable marker sequence can be any sequence that serves these purposes, although typically it will be a sequence encoding a protein that confers a detectable trait on the cell, such as an antibiotic resistance gene or an assayable enzyme not naturally found in the mammalian cell (e.g. β-galactosidase) or a fluorescent protein (e.g. green fluorescent protein, blue fluorescent protein, or a phycobili protein). The marker sequence will also typically contain either a homologous or heterologous promoter that regulates its expression.

The terms "protein", "peptide", and "polypeptide" are used interchangeably herein. As used herein, the phrase "PTTG" refers to a protein member of a mammalian family of PTTG proteins, formerly also known as "pituitary-tumor-specific-gene" (PTSG) proteins, that, for example, are able to transform mammalian cells in tissue culture (e.g., NIH 3T3 and the like).

As used herein, a "promoter region" refers to a segment of DNA that controls transcription of a DNA polynucleotide to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences can be cis acting or can be responsive to trans acting factors.

As used herein, "expression" refers to the process by which polynucleic acids are transcribed into mRNA and translated into peptides, polypeptides, or proteins. If the polynucleic acid is derived from genomic DNA and an appropriate eukaryotic host cell or organism is selected, expression can include splicing of the mRNA.

The term "nucleic acid" encompasses ribonucleic acid (RNA) or deoxyribonucleic acid (DNA), which DNA can be complementary DNA (cDNA) or genomic DNA, e.g. a gene encoding a PTTG protein. "Polynucleotides" encompass nucleic acids containing a "backbone" formed by phosphodiester linkages between ribosyl or deoxyribosyl moieties.

A polynucleotide sequence complementary to a PTTG-specific polynucleotide sequence, as used herein, is one binding specifically or hybridizing with a PTTG-specific nucleotide base sequence. The phrase "binding specifically" or "hybridizing" encompasses the ability of a polynucleotide sequence to recognize a complementary base sequence and to form double-helical segments therewith via the formation of hydrogen bonds between the complementary base pairs. Thus, a complementary sequence includes, for example, an antisense sequence with respect to a sense sequence or coding sequence. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of relatively low stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% sequence identity or homology, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5×SSPE, 0.2% SDS at 42 C, followed by washing in 0.2×SSPE, 0.2% SDS, at 65 C.

The phrase "high stringency hybridization" refers to conditions that permit hybridization of only those nucleic acid sequences that form stable hybrids in 0.018 M NaCl at 65 C (i.e., if a hybrid is not stable in 0.018 M NaCl at 65 C, it will not be stable under high stringency conditions, as contemplated herein). High stringency conditions can be provided, for example, by hybridization in 50% formamide, 5× Denhart's solution, 5×SSPE, 0.2% SDS at 42 C, followed by washing in 0.1×SSPE, and 0.1% SDS at 65 C.

The phrase "low stringency hybridization" refers to conditions equivalent to hybridization in 10% formamide, 5× Denhart's solution, 6×SSPE, 0.2% SDS at 42 C, followed by washing in 1×SSPE, 0.2% SDS, at 50 C. Denhart's solution and SSPE (see, e.g., Sambrook et al., Molecular Cloning, A Laboratory Manual, Cold Spring Harbor Laboratory Press [1989]) are well known to those of skill in the art as are other suitable hybridization buffers.

The term "progeny" or "offspring" refers to animals of any and all future generations derived or descending from a particular rodent, e.g., a rodent ancestor containing one or more targeting vectors inserted or integrated into its genomic DNA, whether the rodent is heterozygous or homozygous for the targeting vector. Progeny of any successive generation are included herein such that the progeny, i.e., the F1, F2, F3, generations, and so on, containing the targeting vector are included in this definition.

Included within the scope of this invention is a rodent in which both of the endogenous PTTG alleles have been artificially mutated, whereby the germ cells of said rodent lack the ability to express functional PTTG protein. Said mutation can be accomplished by various means known in the art, including homologous recombination, transpositional recombination, site directed mutation, and a frame shift mutation within a region or regions of the PTTG gene crucial to expression of a functional PTTG polypeptide. Typically, said mutation is introduced into an embryonic stem cell (ES) or a germ cell, such as an oocyte or male germ cell, which is then used to produce a transgenic zygote by mating with a germ cell of the opposite sex. Where the targeting vector is transfected into the genome of a germ cell, the targeted germ cell then can be combined with a germ cell of the opposite sex—which also can be transfected with a targeting vector—in order to obtain a zygote. The uptake of an exogenously supplied nucleic acid segment, such as a targeting vector, will reach male germ cells that are at one or more developmental stages, and will be taken up by those that are at a more receptive stage. The primitive spermatogonial stem cells, known as A0/As, differentiate into type B spermatogonia. The latter further differentiate to form primary spermatocytes, and enter a prolonged meiotic prophase during which homologous chromosomes pair and recombine. Several morphological stages of meiosis are distinguishable: preleptotene, leptotene, zygotene, pachytene, secondary spermatocytes, and the haploid spermatids. The latter undergo further morphological changes during spermatogenesis, including reshaping of their nuclei, the formation of acrosome, and assembly of the tail. The final changes in the spermatozoon take place in the genital tract of the female, prior to fertilization. The male germ cells can be modified in vivo using gene therapy techniques, or in vitro using a number of different transfection strategies. (E.g., WO 00/69257).

In a preferred embodiment, the mutation is introduced by homologous recombination between at least one of the cell's endogenous copies of the PTTG gene using a targeting vector, where the targeting vector is transfected into the ES cell's genome. The ES cell then can be injected into a blastocyst. The resulting recombinant blastocyst or zygote, as the case may be, can be implanted into a pseudopregnant host, representing the F0 generation. The F1 progeny then can be screened for the presence of one or more mutant PTTG allele. If no PTTG −/− offspring are detected, then the PTTG +/− offspring of the F1 generation can be mated, wherein a predicted about one fourth of the F2 progeny will bear the PTTG −/− genotype, which can be confirmed, for example, using genomic analysis techniques known in the art, such as, e.g., Southern blotting.

In a preferred embodiment, the PTTG null mutant rodent can be generated by homologous recombination with a targeting vector as follows.

A PTTG targeting vector typically is prepared by isolating a genomic PTTG or cDNA PTTG polynucleotide sequence fragment and inserting a selectable genetic marker, typically comprised of an exogenous polynucleotide sequence, into said genomic or cDNA PTTG fragment. The PTTG gene or gene fragment to be used in preparing the targeting vector can be obtained in a variety of ways.

A naturally occurring genomic PTTG polynucleotide sequence fragment or cDNA molecule to be used in preparing the targeting vector can be obtained using methods well known in the art such as described by Sambrook et al. (*Molecular Cloning: A Laboratory Manual*, Cold Spring Harbor Laboratory Press, Cold Spring Harbor, N.Y. [1989]). Such methods include, for example, PCR amplification of a particular DNA polynucleotide sequence using oligonucleotide primers, or screening a genomic library prepared from cells or tissues that contain the PTTG gene with a cDNA probe encoding at least a portion of the same or a highly homologous PTTG gene in order to obtain at least a portion of the PTTG genomic polynucleotide sequence. Alternatively, if a cDNA sequence is to be used in a targeting vector, the cDNA can be obtained by screening a cDNA library (preferably one prepared from tissues or cells that express the PTTG genomic sequence, where the tissues or cells are derived from the same or similar species of mammal as the targeted species) with oligonucleotide probes, homologous cDNA probes, or antibodies (where the library is cloned into an expression vector). In a preferred embodiment, the PTTG gene can be isolated from a mouse 129 SvEv λ genomic library (Stratagene) using a PTTG cDNA probe labeled with a commercially available labeling kit. (Wang, Z., et al., *Characterization of the murine pituitary tumor transforming gene (PTTG) and its promoter*, Endocrinology 141:763–771 [2000]).

In instances where the DNA sequence of the subject endogenous gene is known (as is the case with respect to human, rat, and murine PTTG) a DNA polynucleotide sequence fragment encoding the pertinent portion of said gene can be manufactured synthetically, using chemical synthesis methods such as those described by Engels et al., (Angew. Chem. Int. Ed. Engl., 28:716–734 [1989]), to wit, the phosphoramidite, phosphotriester, and H-phosphonate methods of nucleic acid synthesis. Because the aforementioned nucleic acid chemical synthesis methods only can be used to synthesize polynucleotide sequences of up to about 100 base pairs, and the desired genomic DNA polynucleotide sequence fragments are typically comprised of at least several hundred base pairs, the desired genomic DNA polynucleotide fragment can be synthesized in a number of 100 bp fragments which can then be ligated together using standard DNA ligation methods known in the art.

The PTTG genomic DNA fragment or PTTG cDNA molecule prepared for use in the targeting vector should be generated in sufficient quantity for genetic manipulation. Amplification can be conducted by 1) placing the fragment into a suitable vector and transforming bacterial or other cells that can rapidly amplify the vector, 2) by PCR amplification, 3) by synthesis with a DNA synthesizer, or 4) by other suitable methods now known or later discovered.

The genomic PTTG polynucleotide sequence fragment, cDNA molecule, or PCR-generated fragment for incorporation into the PTTG targeting vector (referred to herein as "the PTTG polynucleotide sequence portion of the targeting vector") can be digested with one or more restriction endonucleases selected to cut at a restriction site(s) also present in the selectable marker sequence, such that the selectable marker sequence can be inserted into a desired position within the PTTG polynucleotide sequence portion of the targeting vector. That is, the selectable marker sequence is inserted into a position along the PTTG polynucleotide sequence portion of the targeting vector, such that, were the selectable marker sequence inserted into the chromosomal copy of the PTTG gene of a particular cell that typically expresses PTTG protein, functional PTTG protein would not be expressed in said cell. The particular position will vary depending on a number of factors, including the available restriction sites in the PTTG polynucleotide DNA sequence fragment into which the selectable marker sequence is to be inserted, whether an exon sequence or a promoter sequence, or both is (are) to be interrupted, and whether several isoforms exist in the mammal (due to alternative splicing) and only one such isoform is to be disrupted. After the PTTG polynucleotide sequence portion of the targeting vector has been digested and the selectable marker sequence inserted therein, the selectable marker sequence should be flanked by at least about 200 polynucleotide base pairs remaining from the digested PTTG polynucleotide sequence portion of the targeting vector. This way, the flanking portions can hybridize with a targeted chromosomal PTTG gene on either side of the desired site of insertion of the selectable marker sequence into the chromosomal PTTG gene. In any event, the exogenous selectable marker sequence should be flanked by polynucleotide sequences, complimentary to the sense strand of the chromosomal PTTG gene, that are of sufficient length to facilitate hybridization with the targeted chromosomal PTTG gene, in order to achieve the desired homologous recombination between nucleotides in the targeting vector and at least one copy of the chromosomal copy of the PTTG gene.

Preferably, the endonuclease(s) selected for digesting the PTTG polynucleotide sequence portion of the targeting vector will generate a longer arm and a shorter arm, where the shorter arm is at least about 300 base pairs (bp). In some cases, it will be desirable to actually delete a portion or even all of one or more introns or exons of the PTTG polynucleotide sequence portion of the targeting vector. In these cases, the PTTG polynucleotide sequence portion of the targeting vector can be cut with appropriate restriction endonucleases such that a fragment of the appropriate size and location can be removed provided that the selectable marker sequence inserted therein is flanked by at least about 200 polynucleotide base pairs complementary to polynucleotide regions of the targeted endogenous PTTG gene at the preferred site of the desired homologous recombination event.

In a most preferred embodiment, the PTTG polynucleotide sequence portion of the targeting vector for incorporation into the PTTG targeting vector contains a deletion of about 4.2 kb, including the translation start site and KOZAK sequences, wherein introduction of such a deletion into the chromosomal copy of the PTTG will eliminate translation of PTTG mRNAs.

The selectable marker sequence used in the targeting vector can be any nucleic acid molecule that is detectable and/or assayable after it has been incorporated into the genomic DNA of an ES or germ cell, and ultimately the null mutant rodent. Expression or presence in the genome or lack thereof can easily be detected by conventional means, as further described herein. Preferably, the selectable marker sequence encodes a polypeptide that does not naturally occur in the mammal. The selectable marker sequence is usually operably linked to its own promoter or to another strong promoter such as the thymidine kinase (TK) promoter or the phosphoglycerol kinase (PGK) promoter from any source that will be active or can easily be activated in the cell into which it is inserted; however, the selectable marker sequence need not have its own promoter attached, as it can be transcribed using the promoter of the gene to be mutated. In addition, the selectable marker sequence will normally have a polyA sequence attached to its 3' end; this sequence serves to terminate transcription of the selectable marker sequence. Preferred selectable marker sequences are any antibiotic resistance gene, such as neo (the neomycin resistance gene), or a bacterial gene, such as beta-gal (beta-galactosidase).

After the PTTG polynucleotide sequence portion of the targeting vector has been digested with the appropriate restriction enzyme(s), the selectable marker sequence molecule can be ligated with the PTTG polynucleotidal sequence portion of the targeting vector using methods well known to the skilled artisan and described in Sambrook et al., supra. In some cases, it will be preferable to insert the selectable marker sequence in the reverse or antisense orientation with respect to the PTTG nucleic acid sequence; this reverse insertion is preferred where the selectable marker sequence is operably linked to a particularly strong promoter.

The ends of the DNA molecules to be ligated must be compatible; this can be achieved by either cutting all fragments with those endonucleases that generate compatible ends, or by blunting the ends prior to ligation. Blunting can be done using methods well known in the art, such as for example by the use of Klenow fragments (DNA polymerase I) to fill in sticky ends. After ligation, the ligated constructs can be screened by selective restriction endonuclease digestion to determine which constructs contain the marker sequence in the desired orientation.

The ligated DNA targeting vector then can be transfected directly into embryonic stem cells (discussed below) or germ cells, or it can first be placed into a suitable vector for amplification prior to insertion. Preferred vectors are those that are rapidly amplified in bacterial cells such as the pBluescript II SK vector (Stratagene, San Diego, Calif.) or pGEM7 (Promega Corp., Madison, Wis.).

The PTTG targeting vector is typically transfected into stem cells derived from an embryo (embryonic stem cells, or "ES cells"). ES cells are undifferentiated cells that are capable of differentiating into and developing into all cell types necessary for organism formation and survival. Generally, the ES cells used to produce the null mammal will be of the same species of rodent as the null mutant rodent to be generated. Thus for example, mouse embryonic stem cells will usually be used for generation of null mice.

The embryonic stem cell line used is typically selected for its ability to integrate into and become part of the germ line of a developing embryo so as to create germ line transmission of the targeting vector. Thus, any ES cell line that is believed to have this capability is suitable for use herein. Preferred ES cell lines for generating null mice are murine cell lines J1 ES cells (UCLA ES Cell Center). The cells are cultured and prepared for DNA insertion using methods well known to the skilled artisan such as those set forth by Robertson (in: *Teratocarcinomas and Embryonic Stem Cells: A Practical Approach*, E. J. Robertson, ed. IRL Press, Washington, D.C. (1987)), by Bradley et al. (Current Topics in Devel. Biol., 20:357–371 (1986)) and by Hogan et al. (*Manipulating the Mouse Embryo: A Laboratory Manual*, Cold Spring Harbor Laboratory Press, Cold Spring Harbor, N.Y. (1986)).

Insertion (also termed "transfection") of the targeting vector into the ES cells or germ cells can be accomplished using a variety of methods well known in the art including for example, electroporation, microparticle bombardment, microinjection, viral transduction, and calcium phosphate treatment (see Lovell-Badge, in Robertson, ed., supra). A preferred method of insertion is electroporation.

The PTTG targeting vector to be transfected into the cells can first be linearized if the targeting vector has previously been inserted into a circular vector. Linearization can be accomplished by digesting the DNA with a suitable restriction endonuclease selected to cut only within the vector sequence and not within the targeting vector sequence.

The isolated PTTG targeting vector can be added to the ES cells or germ cells under appropriate conditions for the insertion method chosen. Where more than one targeting vector is to be introduced into the cells, the DNA molecules encoding each such vector can be introduced simultaneously or sequentially. Optionally, homozygous PTTG null ES cells can be generated by adding excessive PTTG targeting vector DNA to the cells, or by conducting successive rounds of transfection in an attempt to achieve homologous recombination of the targeting vector on both endogenous PTTG alleles.

If the ES cells or germ cells are to be electroporated, the cells and targeting vector DNA are exposed to an electric pulse using an electroporation machine and following the manufacturer's guidelines for use. After electroporation, the cells are typically allowed to recover under suitable incubation conditions. The cells are then screened for the presence of the targeting vector.

Screening the transfected cells can be accomplished using a variety of methods, but typically, one screens for the presence of the selectable marker sequence portion of the targeting vector. Where the selectable marker sequence is an antibiotic resistance gene, the cells can be cultured in the presence of an otherwise lethal concentration of antibiotic. Those cells that survive have presumably integrated the targeting vector. If the selectable marker sequence is other than an antibiotic resistance gene, a Southern blot of the ES cell genomic DNA can be probed with a sequence of DNA designed to hybridize only to the marker sequence. If the selectable marker sequence is a gene that encodes an enzyme whose activity can be detected (e.g., beta-galactosidase), the enzyme substrate can be added to the cells under suitable conditions, and the enzymatic activity of the selectable marker sequence can be analyzed.

The targeting vector can integrate into several locations in the ES cell or germ cell genome, and can integrate into a different location in each cell's genome, due to the occurrence of random insertion events. The desired location of insertion is within a region of the PTTG endogenous gene sequence that eliminates functional PTTG protein expression. Typically, less than about 1–10 percent of the cells that take up the targeting vector will actually integrate the targeting vector in the desired location. To identify those cells with proper integration of the targeting vector, chromosomal DNA can be extracted from the cells using standard methods such as those described by Sambrook et al., supra. The extracted DNA then can be probed on a Southern blot with a probe or probes designed selectively to hybridize to the targeting vector digested with (a) particular restriction enzyme(s). Alternatively, or additionally, a specific genomic DNA sequence can be amplified by PCR with probes specifically designed to amplify that DNA sequence such that only those cells containing the targeting vector in the proper position will generate DNA fragments of the proper size.

After suitable ES cells containing the targeting vector in the proper location have been identified, the transformed ES cells can be incorporated into an embryo. Incorporation can be accomplished in a variety of ways. A preferred method of incorporation of ES cells is by microinjection into an embryo that is at the blastocyst stage of development. For microinjection, about 10–30 cells are collected into a micropipet and injected into a blastocyst to integrate the ES cell into the developing blastocyst.

The suitable stage of development for the blastocyst is species dependent, however for mice it is about 3.5 days. The blastocysts can be obtained by perfusing the uterus of pregnant females. Suitable methods for accomplishing this are known to the skilled artisan, and are set forth for example by Bradley (in Robertson, ed., supra).

While any blastocyst of the right age/stage of development is suitable for use, preferred blastocysts are male and have genes coding for a coat color or other phenotypic marker that is different from the coat color or other phenotypic marker encoded by the targeted ES cell genes. In this way, the offspring can be screened easily for the presence of the targeting vector by looking for mosaic coat color or other phenotypic marker (indicating that the ES cell was incorporated into the developing embryo). Thus, for example, if the targeted ES cell line carries the genes for white fur, the embryo selected will preferably carry genes for black or brown fur.

After the ES cells have been incorporated, the transfected embryo can be implanted into the uterus of a pseudopregnant host. While any pseudopregnant host can be used, preferred hosts are typically selected for their ability to breed and reproduce well, and for their ability to care for their young. Such pseudopregnant hosts are typically prepared by mating with vasectomized males of the same species. The pseudopregnant stage of the host mother is important for successful implantation, and it is species dependent. For mice, this stage is about 2–3 days pseudopregnant.

As an alternative means to transfection of the targeting vector into an embryonic stem cell, the targeting vector can be transfected into a rodent germ cell, i.e., an oocyte or murine germ cell. Typically, retroviral vectors have been utilized to generate transgenic organisms by transfection of the viral vector into oocytes (Chan, A. W., et al., *Transgenic Cattle produced by Reverse-Transcribed Gene Transfer in Oocytes*, Proc. Natl. Acad. Sci. USA 95:14028–14033 [1998]). Transgenic mice also were produced after the injection of exogenous DNA together with sperm heads into oocytes (Perry, A. C., et al., *Alien Transgenesis by Intracytoplasmic sperm injection*, Science 284 1183 [1999].

Transgenic mammals also can be generated in vivo and in vitro (ex vivo), for example, by transfection, transduction, microparticle bombardment, or electroporation of vertebrate animal germ cells with the targeting vector together with a suitable transfecting agent. The in vivo method involves injection of the targeting vector directly into the testicle of the animal. In this method, all or some of the male germ cells within the testicle are genetically modified in situ, under effective conditions. The in vitro method involves obtaining germ cells from the gonad (i.e., testis) of a suitable donor or from the animal's own testis, using a novel isolation or selection method, transfecting or otherwise genetically altering them in vitro, and then returning them to the substantially depopulated testis of the donor or of a different recipient male vertebrate under suitable conditions where they will spontaneously repopulate the depopulated testis.

The in vitro method has the advantage that the transfected germ cells can be screened by various means before being returned to the testis of the same or a different suitable recipient male to ensure that the transgene is incorporated into the genome in a stable state. Moreover, after screening and cell sorting only enriched populations of germ cells can be returned. These methods are more fully described in, for example, PCT/US98/24238.

Then, the male vertebrate is mated with a female vertebrate of its species, and the progeny then are screened for transgenic animals.

Offspring that are born to the host mother can be screened initially for mosaic coat color or other phenotype marker where the phenotype selection strategy (such as coat color, as described above) has been employed. In addition, or as an alternative, chromosomal DNA obtained from tail tissue of the offspring can be screened for the presence of the targeting vector using Southern blots and/or PCR as described above. The offspring that are positive for the PTTG targeting vector will typically be heterozygous, although some homozygous nulls may exist. Offspring that are homozygous for incorporation of the targeting vector can typically be detected by use of a probe tailored to hybridize with regions common both to the wild-type PTTG gene and the recombinant PTTG gene, such that detection only of the fragment corresponding with the endonuclease restriction fragment predicted for the recombinant PTTG gene will tend to indicate homozygosity for the recombinant gene. Naturally, the success of this approach requires that the technique employed yields polynucleotide products for detection that differ in length depending upon whether or not the targeting vector has been incorporated into the chromosomal copy of the PTTG locus. For example, were genomic analysis performed using the Southern blot technique as described above, the restriction fragments predicted for endonuclease digestion of cells bearing the wild-type PTTG gene as opposed to cells bearing the recombinant PTTG genes must differ in length by an amount capable of being detected on an electrophoretic gel. This way, the transgenic animals that are heterozygous for incorporation of the targeting vector will yield two fragments of differing lengths that hybridize with the probe, while those that are homozygous for the targeting vector will yield fragments of a single length.

If homozygous null mammals are desired, they can be prepared by mating the male and female offspring of the same species, who are believed to carry the targeting vector in their germ line, to each other. Typically, about one fourth of the offspring of such matings will bear the recombinant PTTG allele at both chromosomal copies of the PTTG locus within their germ line cells, i.e., PTTG –/–. If it is unclear whether the offspring will have germ line transmission, they can be mated with a parental or other strain and the offspring screened for –/– PTTG. Animals that are PTTG –/– can be identified by Southern blotting, wherein rodents into whose genome the targeting vector has been incorporated, preferably, will yield restriction fragments of different lengths as compared to the cells of the animals not having incorporated the targeting vector. Probes to screen the Southern blots for the presence of the targeting vector in the genomic DNA can be designed as set forth above. Those skilled in the art will readily appreciate that, although the mutation described herein has been inserted into the germ cells of a parent rodent, the disrupted PTTG gene of the transgenic rodent of the present invention ultimately will be present in the germ cells of future progeny and subsequent generations thereof. In addition, the genetic material is also present in cells of the progeny other than germ cells, i.e., somatic cells.

Other means of identifying and characterizing the null mutant offspring are also available. For example, Northern blots can be used to probe mRNA obtained from various tissues of the offspring for the presence or absence of transcripts encoding either the mutated PTTG gene, the selectable marker sequence, or both. In addition, Western blots can be used to assess the level of expression of PTTG polypeptide product in various tissues of these offspring by probing the Western blot with an antibody against the PTTG protein, or an antibody against the selectable marker sequence protein product.

Also included within the scope of the invention are somatic or germ line cells derived by any means from the null mutant rodent described herein. With respect to germ line cells, such cells can be harvested, isolated selected, removed, extracted, or otherwise obtained from the null mutant rodent of the present invention by conventional means. With respect to the somatic cells, these cells can be used to develop or maintain cell lines. Such cell lines can be derived, obtained, removed from, biopsied, or otherwise disassociated from the null mutant of the present invention and maintained using means known in the art.

It is a further object of the present invention to provide an in vivo animal model for examining the phenotypic consequences resulting from the absence of PTTG protein. The homozygous PTTG null rodents of this invention will have a variety of uses, since PTTG has been implicated in the regulation of cell division, lymphocyte activation, and carcinogenesis, to name a few. As set forth herein, the absence of functional PTTG polypeptide has been implicated in the etiology of various physiological phenomena and medical conditions, including diabetes, hyperglycemia, hypoinsulinaemia, hypoleptinemia, chromosomal aneuploidy, premature centromere division, chromosomal damage, aberrant cell cycle control, thymic hyperplasia, splenic hypoplasia, thrombocytopenia, and female subfertility. Thus, the PTTG null rodent of the present invention will be useful as a mammalian in vivo screening model for studying these and other phenomena.

To this end, PTTG –/– null mice were analyzed for various indicia, including blood and urine glucose levels, body weight, insulin availability, leptin availability, litter size, spleen weights, thymus size, and bleeding time. In addition, PTTG –/– and PTTG +/+ mouse embryonic fibroblasts (MEFs) were observed for the purpose of studying their respective cell cycle control parameters and chromosomal morphology. The fact that only these indicia are described herein should not be understood to mean that the PTTG null mouse of the present invention is useful only in treating or studying these conditions or phenomena. On the contrary, these indicia are offered by way of example only; the far reaching investigative and therapeutic utility of the invention will be apparent to those persons skilled in the art, and are expressly included within the scope of the present invention. By way of example only, PTTG null rodents of the present invention also can be used to study carcinogenesis, T-lymphocyte activation, and promoter transcriptional activation, and signal transduction to name a few.

The invention will be described in greater detail by reference to the following examples. These examples are not to be construed in any way as limiting the scope of this invention.

EXAMPLE 1

Preparation of PTTG Null Rodents

A 16 kb Not I fragment containing the entire PTTG coding region was isolated from a mouse 129 SvEv λ genomic library (Stratagene) using a PTTG cDNA probe labeled using a commercially available labeling kit. (Wang, Z., et al., *Characterization of the murine pituitary tumor transforming gene (PTTG) and its promoter*, Endocrinology 141:763–771 [2000]). The targeting vector contained the equivalent of ~12.5 kb murine PTTG genomic DNA with a 4.2 kb Hind III—EcoR I fragment deletion, including part of the first exon containing the ATG start codon, exons 2 and 3, through the middle of the 3$^{rd}$ intron, replaced with pGK-neo. (FIG. 1A). The targeting vector was then electroporated into *E. coli* DH5 α and propagated. The recombinant plasmid DNA was then extracted and linearized with Not I, electroporated into J1 ES cells derived from mice with agouti fur, and selected in 0.4 mg/ml G418. DNAs from ES cell clones were digested with Hind III and probed with the labeled 345 bp fragment external to the 5' end of the targeting vector shown in FIG. 1A. The probe is set forth in Table 1 (SEQ. ID. NO.: 1). From 800 ES colonies 5 clones were identified with correct homologous recombination by Southern blot analysis. (FIG. 1B). PTTG +/− ES cells were then microinjected into C57BL6 blastocysts possessing black fur, and germline transmission observed in male chimeras exhibiting agouti fur color representing two separate ES cell clones. Chimeras were crossed with C57BL6 strain for the production of knockout mice. Murine offspring were genotyped by either genomic Southern blot as described below or PCR. [For PCR, cycling parameters were 94C 20" 56C 20", and 72C 1' for 30 cycles. Primers PTTG2S (5' GGTTTCAACGCCACGAGTCG 3') (SEQ. ID. NO.: 2) and PTTG1AS (5' CTGGCTTTTCAGTAACGCTGTTGAC 3') (SEQ. ID. NO.: 3) were used for wild-type PTTG detection of a 114 bp fragment; primers GENO1S (5' GTGCTACTTCCATTTGTCACGTCC 3') (SEQ. ID. NO.: 4) and GENO4AS (5' GTGCTACTTCCATTTGT-CACGTCC 3') (SEQ. ID. NO.: 5) were used for targeted PTTG detection of a 596 bp fragment.]

PTTG +/− offspring (F1) were mated and, of the first 100 F2 progeny, 23 were PTTG +/+, 51 were PTTG +/−, and 26 were PTTG −/−, as revealed by Southern and Northern blots. In Southern blot analysis, genomic DNA from ES cells or mice tail were digested with HindIII, electrophoresised in 1% agarose gel and blotted onto Hybond-N membrane (Amersham). The hybridization was performed using QuikHyb (Stratagene) and exposed for radioactivity. The probe was designed to hybridize with nucleotides of the PTTG gene that are 5' external to the targeting vector. (See, e.g., Table 1.) An 1.7 kb hybridizing fragment corresponds to the wild-type PTTG allele, while an about 4.9 kb hybridizing fragment corresponds to the targeted PTTG allele. (FIG. 1B). In Northern blot analysis, total RNA were prepared from mouse tissues using Trizol (Gibco), electrophoresised in 1% formaldehyde denaturing gel and blotted onto Hybond-N membrane. (Sambrook, Joseph, et al., *Molecular cloning: a laboratory manual*, 2nd ed., Cold Spring Harbor, N.Y.: Cold Spring Harbor Laboratory [1989].) A DNA fragment corresponding to mPTTG exon 3 cDNA sequence (372 bp) was used as probe, and GAPDH was used as an internal control. (FIG. 1C). As PTTG exons 2 and 3 were deleted from the PTTG genetic material that comprises the targeting vector, the absence of hybridization of the probe with mRNA prepared from tissue of a particular recombinant mouse evidences that said mouse contains the targeting vector incorporated into the proper position of the mouse's genome. RT-PCR and sequencing analysis showed that the KOZAK sequence was absent from the mRNAs of the transgenic mice, therefore no derived translation product was predicted in such mice.

TABLE 1

Southern Blot Hybridization Probe (SEQ. ID. NO. 1)
5' CACCAG TCACACATCA GCATCTCCTG TGGCTCCATA

GAGCTGAGGA CTTTACAAGC TGTCACAACC TTTGTAGAAA

GGGTCTGTCC AGCAGGAGGG GGTGGGGTGG GGTGGGTGAA

ATTCCTAGTA CAAGTATCCC AGTATCAATC ATGGAACTTT

AGAATGTTTT CAGGAACACA CAAAGGAGAC TAAGG 3'.

EXAMPLE 2

Figure 2:
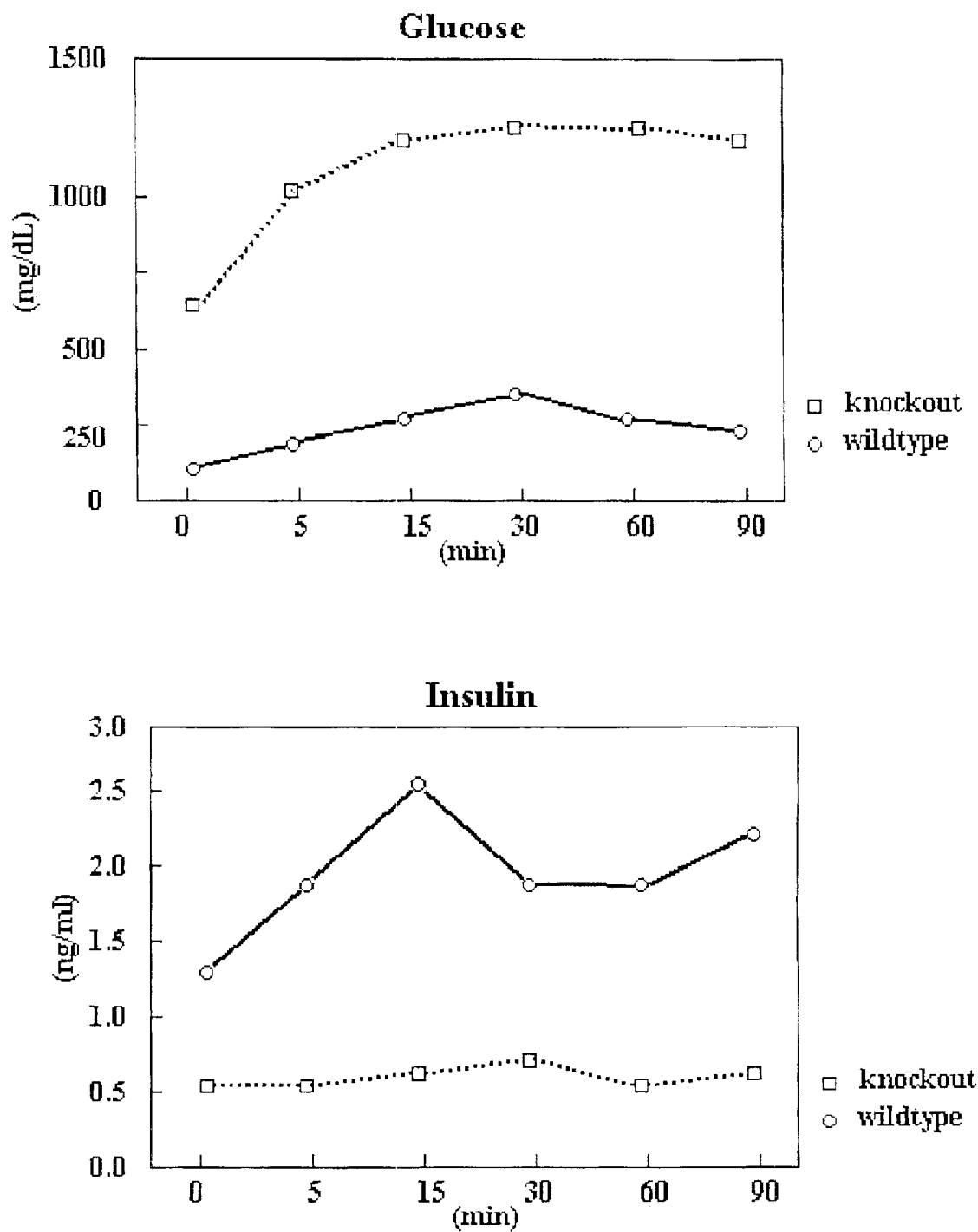
FIG. 2 demonstrates an impaired glucose response in PTTG −/− mice. 10 male PTTG −/− mice and 6 male PTTG +/+ mice were fasted 16–20 hrs before glucose injection (1 g/kg weight) i.p., blood samples were collected at indicated timepoints after injection. Insulin was measured using a Ultrasensitive rat insulin ELISA kit (Crystal Biochem, Chicago, Ill.) and glucose measured using DEX glucometer (Bayer). PTTG −/− and PTTG +/+ samples are indicated.

Diabetes Study with PTTG Null Mutant Rodents
Blood Glucose Assay:
Method
18 male and 15 female PTTG null mice and 10 male and 12 female wild-type control mice were fasted 16–20 hrs before blood was collected and used for glucose assay using DEX glucometer (Bayer) per manufacturer's instructions.
Results
Hyperglycemia, hypoinsulinaemia and hypoleptinemia was observed in male PTTG null mice at 2 months old, which became more prominent after 5–6 months. Only 1 out 15 female PTTG null mice showed hyperglycemia at 12 months age. No hyperglycemia or hypoinsulinaemia was observed in the wild-type male or female mice of the control group. At 9 months old, above 80% (11 out of 13 male mice observed) had hyperglycemia (blood glucose level at 800 mg/dL±250 mg/dL in fasted PTTG knockout male mice vs. 70 mg/dL±15 mg/dL in control), hypoinsulinaemia (0.3 ng/ml±0.12 ng/ml in PTTG knockout mice vs. 1.6 ng/ml±0.4 ng/ml in control group), and hypoleptinemia (circulating leptin levels at 6.3 ng/ml±0.5 ng/ml in PTTG −/− males vs. 41.5 ng/ml±4.2 ng/ml in controls). These PTTG knockout male mice also had reduced body weight (32.2 g±5.1 g in PTTG knockout mice vs. 48.4 g±5.8 g in wild-type control group).
Glucose Tolerance Assay:
Method
10 male PTTG null mice and 6 male wild-type mice were fasted 16–20 hrs before injection of glucose (1 g/kg weight) i.p., and then blood was collected at timepoints 0, 5, 15, 30, 60 and 90 minutes. Both glucose levels and insulin levels were measured. Insulin assays were performed using a Ultrasensitive rat insulin ELISA kit from Crystal Biochem (Chicago, Ill.).
Results
PTTG knockout male mice demonstrated much less insulin secretory sensitivity to the increase in blood glucose as compared to wild type mice. (See FIG. 2, where the null mutant rodents shows high blood glucose levels [approx. 600–1250 mg/dL] and low blood insulin levels [approx. 0.6 ng/ml], relative to the wild-type mice [approx. 200 mg/dL and 1.3–2.5 ng/ml, respectively], over the same period).
Urine Glucose and Ketone Analysis:
Methods
13 male PTTG null mice and 10 male wild-type mice were fasted 16–20 hrs before urine collection. The urine glucose and ketone analysis were performed using Keto-Diastix Reagent Strips (Bayer) per manufacturer's instructions.
Results
11 out of 13 male PTTG null mice show urine glucose >1000 mg/dL, while none of the 10 wild-type mice show detectable level of urine glucose.

Pancreas Pathology and Histology Analysis:

Methods

Pancreases were collected from 4 male PTTG null mice and 4 male wild-type and histology analyses were performed using standard methods.

Results

Figure 3:
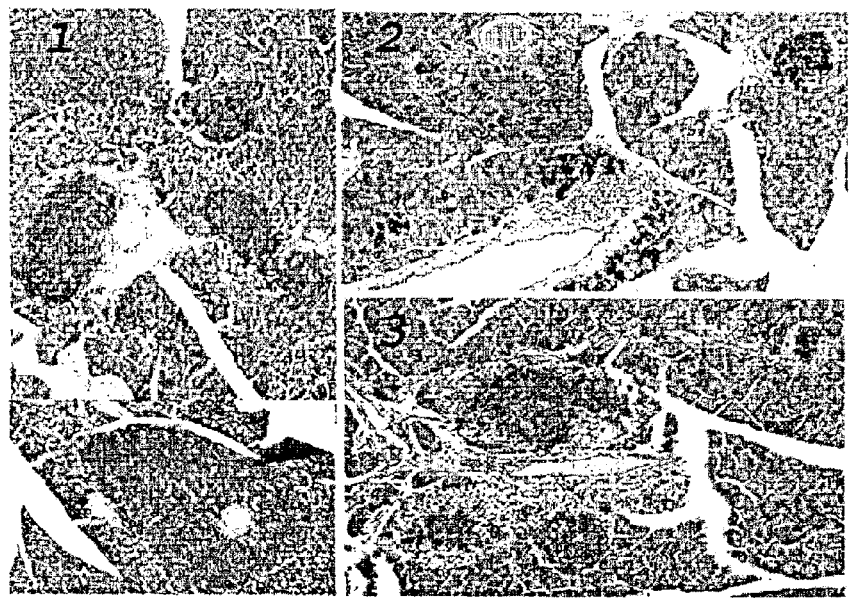
FIG. 3 depicts immunohistology and pathology analyses of PTTG +/+ and PTTG −/− mouse pancreases.
Figure 3:
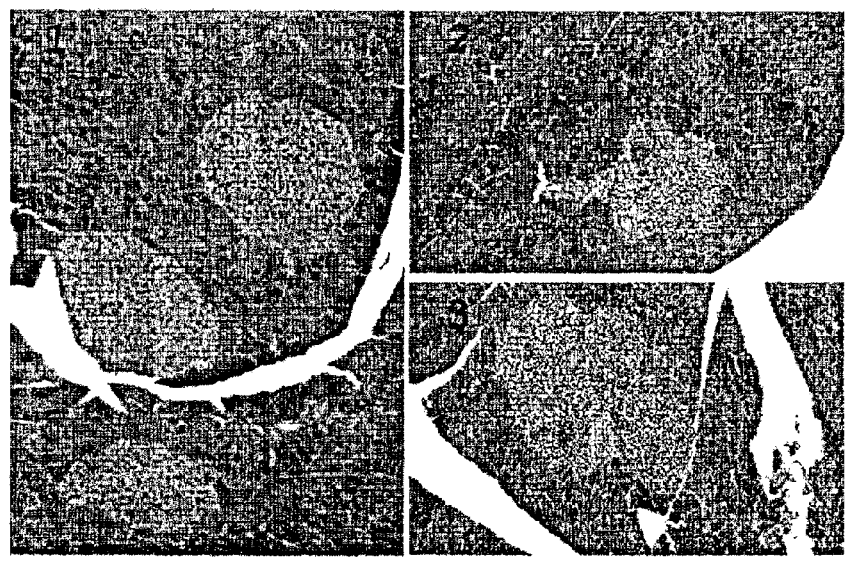

Insulin immunostaining showed significantly reduced insulin level in pancreatic islet cells in PTTG knockout male mice as compared with wild-type controls. (See FIG. 3A, where cells showing up in dark shade represent insulin-secreting cells, which are significantly more prevalent in the PTTG +/+ pancreas [Panel 1], than the PTTG −/− pancreases [Panels 2 and 3]). In addition, lymphocyte infiltration, a hallmark of autoimmune reactivity, was observed in the pancreases of male PTTG null mice. (See FIG. 3B, where there is a high percentage occupance of lymphocytes (the darkly shaded dots) in islets in the PTTG −/− pancreases [Panels 2 and 3], rather than PTTG +/+ pancreas [Panel 1].

Cumulatively, the results set forth in this example strongly suggest that male PTTG null mice have diabetes. It should also be noted that, in contrast to non-obese diabetes (NOD) mice—one established diabetes mouse model—PTTG null mice have a higher diabetes occurrence in male (>50% at 25 weeks, >80% at 45 weeks), than in their female counterparts (0 at 30 weeks, 5% over 53 weeks). In NOD mice, the occurrence of diabetes in female mice (>80% at 30 weeks), than in male mice (~40% at 30 weeks). Thus, it appears that the sexual dimorphism of the disease occurrence in PTTG null mice is drastically different from that in NOD mice. Moreover, while NOD mice exhibit a polygenic contribution to the occurrence of diabetes, diabetes in PTTG null mice appear to result from a single gene disruption. In addition, in steptozotocin (STZ) treated mice—STZ is a compound harmful to the pancreas—develop diabetic symptoms through an unknown mechanism. Unlike these established diabetic mouse models, the present invention, which provides a PTTG mouse model to study diabetes generated through a single gene locus, can serve as an effective model for screening drug candidates for treating and preventing diabetes, and for studying the etiology of diabetes in general.

EXAMPLE 3

Female Fertility Study with PTTG Null Mutant Rodents

Method

To determine what effect, if any, PTTG under-expression can have on mouse litter size, the average litter size was measured from 15 breedings using mice bearing the PTTG −/− genotype.

Results

The average litter size of the PTTG −/− matings were less than half that of the litter size from a PTTG +/− or +/+ dam, 3–5 versus 7–11 pups/litter, respectively. (Table 2) This indicated that the PTTG −/− mice are viable and fertile, but demonstrate female subfertility.

Moreover, the fact that matings of +/− mice yields progeny in a ratio of about 1:2:1 ratio of PTTG +/+:+/−:−/−, as set forth in Example 1, implies that PTTG deficiency did not result in significant mortality during intra-uterine development.

TABLE 2

Litter Sizes in Breeding Pairs

|       | M(+/+)      | M(+/−)      | M(−/−)      |
| ----- | ----------- | ----------- | ----------- |
| F(+/+) | 8.6 ± 2.1  | n/a         | 8.1 ± 1.8   |
| F(+/−) | n/a        | 7.8 ± 1.6   | 7.7 ± 1.6   |
| F(−/−) | 4.2 ± 1.1  | 4.2 ± 1.6   | 3.8 ± 1.0   |

These results were obtained from at least 3 breeding pairs except for M(+/+)×F(+/+) or M(−/−)×F(−/−) where 15 breeding pairs were used.

EXAMPLE 4

Thrombocytopenia Study with PTTG Null Mutant Rodents

Method

Blood samples from six PTTG −/− and six PTTG +/+ mice were collected for hematological analysis including whole blood counting, blood and bone marrow smears. Femurs were used to make sections for morphological observation and megakaryocyte counting. Standard histological analysis was used as described in Brown, Geoffrey G. An introduction to histotechnology: a manual for the student, practicing technologist, and resident-in-pathology/, Geoffrey G. Brown: foreword by John M. Budinger. New York: Appleton-Century-Crofts, [c1978]. Bleeding time was measured as described in Offermanns, S., et al., *Defective platelet activation in G alpha(q)-deficient mice*, Nature, 387:183–186 [1997].

Results

Figure 4:
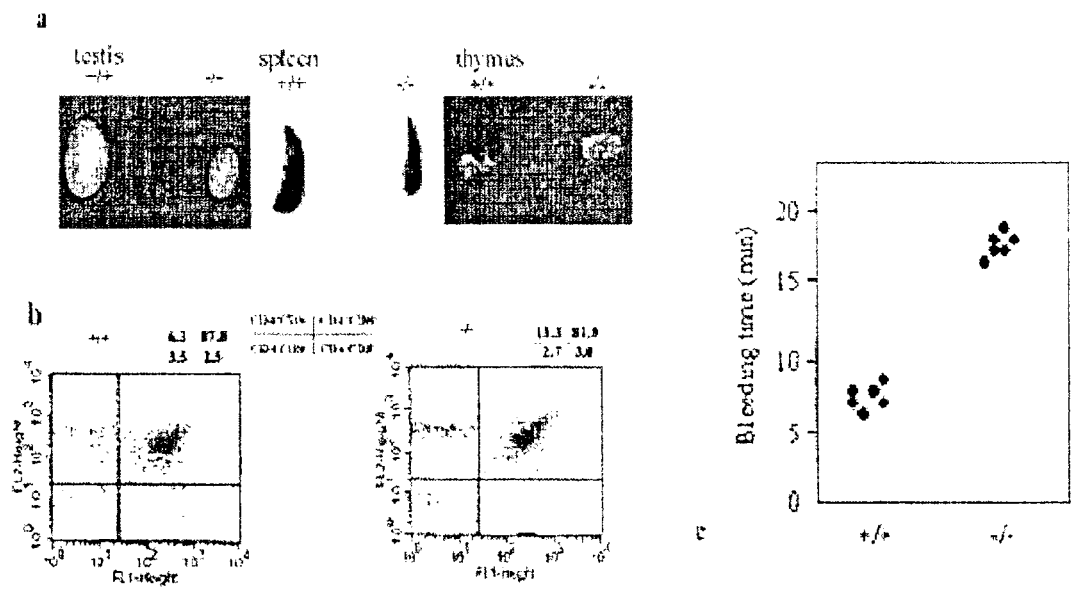
FIG. 4 depicts hematopoietic and immunologic analysis in PTTG +/+ and PTTG −/− mice.

Hematological analysis showed that PTTG −/− mice are thrombocytopenic, despite normal numbers of bone marrow megakaryocytes. PTTG −/− platelet numbers ranged from 40–65% of PTTG +/+ mice and PTTG −/− bleeding time was prolonged (16–19 minutes vs. 5–10 minutes in PTTG +/+ mice, P<0.005) (FIG. 4C).

EXAMPLE 5

Cell Cycle Control Study with Murine Embryonic Fibroblasts

Method

PTTG +/+ and −/− murine embryonic fibroblasts (MEFs) were prepared from embryos that advanced 13.5 days from the copulation event (E13.5 embryos) respectively as described (Patel, K. J., et al., *Involvement of Brca2 in DNA repair*, Mol. Cell. 1:347–357 [1998]), and maintained in DMEM with 10% fetal bovine serum. Cells at passage 3–5 were plated at $4 \times 10^5$ per 60 mm dish, and either irradiated (12 Gy) from a 137Cs Gammacell 40 irradiator or DMEM added with 0.1% fetal bovine serum in separate experiments. Cells were harvested at the indicated times for cell cycle analysis.

Cells were trypsinized at the indicated times, washed with PBS, resuspended in 1 ml PBS, fixed with 2 ml cold methanol, treated with propidium iodide (PI) and Rnase A and subjected to cell cycle analysis using FACS-Star (Becton Dickinson).

For retroviral transfection experiments, a retroviral plasmid pLPCX-PTTG was generated by subcloning murine PTTG cDNA into pLPCX (Clontech) via EcoR I and Not I sites. A viral packaging cell line Eco293 was purchased from Clontech. Retrovirus were produced by transfecting pLPCX-PTTG into Eco293 cells and harvesting supernants 48 hours after transfection. The viral titers were between $5 \times 10^5$/ml to $1 \times 10$/ml. PTTG +/+ and -/- cells were then infected with PTTG expression retrovirus and subjected to cell cycle analysis.

Results

Figure 5:
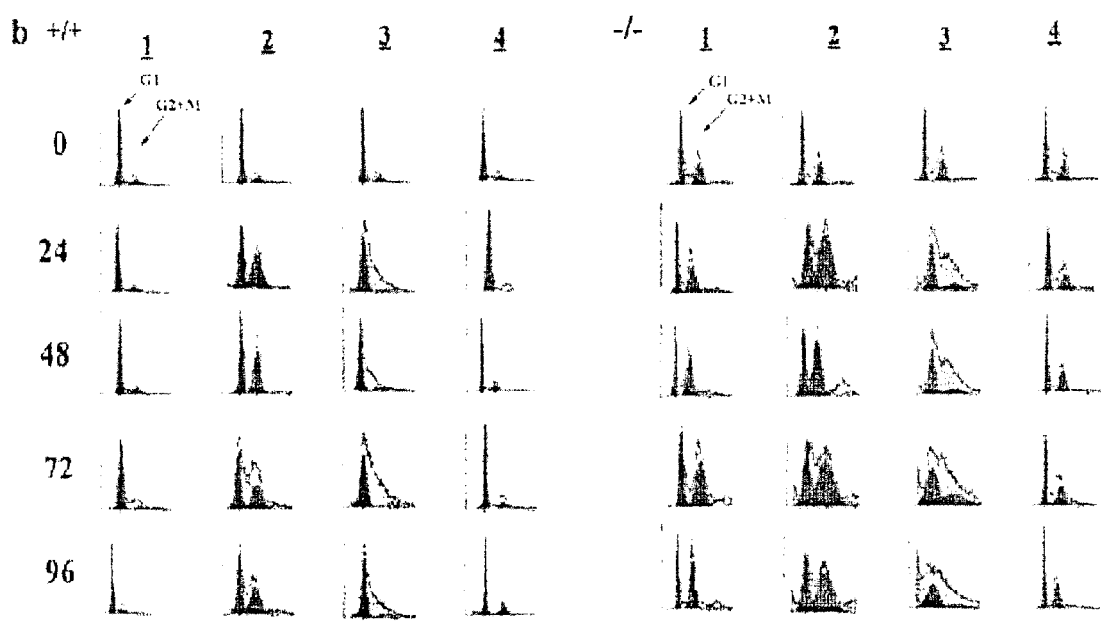
FIG. 5 depicts the results of a representative cell cycle analysis of PTTG +/+ and PTTG −/− Murine Embryonic Fibroblasts (MEFs). In the experiment illustrated in FIG. 5A, PTTG +/+ and PTTG −/− MEFs were plated at low ($4\times10^3/cm^2$), medium ($8\times10^3/cm^2$) and high ($1.6\times10^4/cm^2$) concentrations respectively, and cell doubling times and cell cycle parameters assessed as previously described. (Sell, C., et al., *Effect of a null mutation of the insulin-like growth factor I receptor gene on growth and transformation of mouse embryo fibroblasts*, Mol. Cell. Biol. 14:3604–3612 [1994]) Doubling time determined in this experiment was 30.6 hrs for PTTG +/+ cells and 29.8 hrs for PTTG −/− cells. The length of time (hrs) an average cell spends in the cell cycle phases is indicated.

PTTG -/- and PTTG +/+ mouse embryonic fibroblasts (MEFs) both derived at passage 3 demonstrated similar doubling times (~30 hrs) but different cell cycle parameters (FIG. 5A). The PTTG -/- MEF G1 phase was shortened (10.1 vs. 18.2 hrs), with a prolonged G2-M phase (7.2 vs. 1.4 hr), implying deficient $G_0$-G1 checkpoint control and delayed progression of G2-M. PTTG -/- MEFs showed a flow cytometric pattern similar to a pattern in a DNA damaged cell population such as one observed in γ-irradiated WT PTTG +/+ MEFs (FIG. 5A). Untreated PTTG +/+ MEFs exhibit 62–75% in $G_0$-G1, 15–27% in S and 3–10% in G2-M phases respectively during 96 hr observation. In contrast, 37–54% of PTTG -/- MEFs were in the $G_0$-G1 phase, 13–32% in S phase and 27–43% in the G2-M phase (FIG. 5B). After γ-irradiation, the number of PTTG +/+ MEFs in G2-M phase increased to 28–51%, while 45–62% of PTTG -/- MEFs were in the G2-M phase (FIG. 5B), implying that the G2-M checkpoint is functional in both γ-irradiated PTTG +/+ and PTTG -/- MEFs (FIG. 5B).

Interestingly, introduction of PTTG into PTTG -/- MEFs via retroviral transfection substantially increased the number of cells in S phase (~40% at 72 hr vs. 19% at baseline) while reducing the number of cells in G2-M (~10% at 72 hr vs. ~29% at baseline) (FIG. 5B), reflecting phenotype reversal of PTTG -/- MEF cells showing a large G2-M phase. Moreover, more than 85% PTTG +/+ MEFs were in $G_0$-G1 after 96 hr serum starvation, while only 65% PTTG -/- MEFs were in $G_0$-G1 with >20% PTTG -/- MEFs still residing in G2-M after serum starvation (FIG. 5B).

Results

EXAMPLE 6

Nuclear and Chromosomal Study with Murine Embryonic Fibroblasts

Method

For nuclear analysis, PTTG +/+ and -/- MEFs grown on chamber slides were immunostained with anti-α-tubulin and Rhamine-anti-goat secondary antibody, and counterstained with Hoescht 33258. (Yu, R., et al., Pituitary tumor transforming gene causes aneuploidy and p53-dependent and p53-independent apoptosis, J. Biol. Chem. 275:36502–36505 [2000]). For chromosome analysis, Mitotic MEFs were collected after 16 hr colcemid treatment (50 ng/ml), hypotonized and fixed with cold Carnoy's fixative. Fixed cells were then dropped onto slides and processed by standard cytogenetic procedures. (*The AGT cytogenetics laboratory manual*, 3rd edition, Lippincott-Raven Publishers, Philadelphia [1997]). Chromosome number and gross rearrangements were determined in at least 50 metaphase cells.

Results

Figure 6:
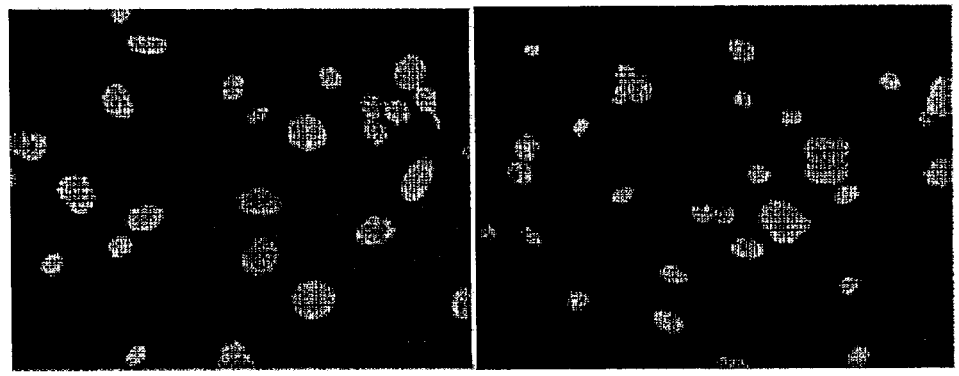
FIG. 6 depicts abnormal nuclear and chromosome morphology in PTTG −/− MEFs.
Figure 6:
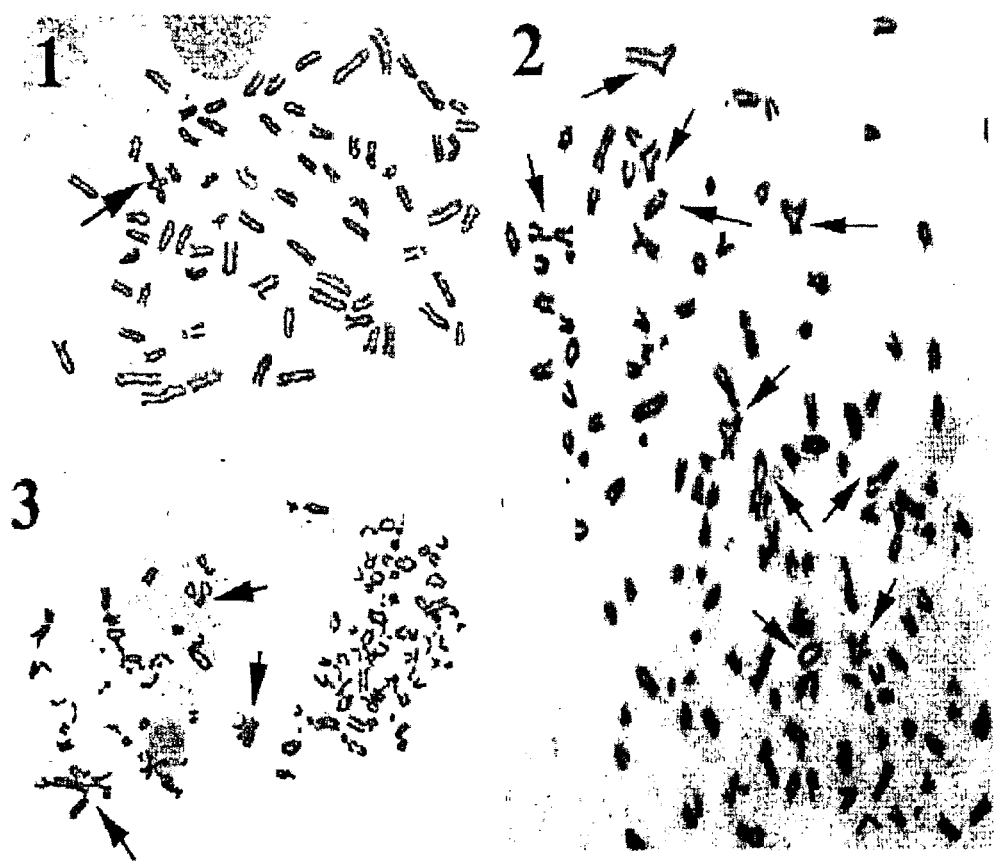

PTTG -/- MEFs demonstrated disordered cell nuclear morphology and about 12–15% PTTG -/- MEFs are binucleated or multinucleated vs. <1% of PTTG +/+ MEFs (FIG. 6A). PTTG -/- MEFs demonstrated enhanced aneuploidy and several aberrant chromosome morphologies (FIG. 6B). 10–15% of PTTG -/- MEFs were aneuploid versus ~1% of PTTG +/+ MEFs, and aberrant chromosome morphologies, including quadriradials, triradials and breaks were observed in 4–6% of PTTG -/- metaphase spreads examined, while no such anomalies were observed in PTTG +/+ MEFs. The binucleated and multinucleated cells probably contribute to the observed higher percentage of PTTG -/- MEFs in G2-M as assessed by flow cytometry, as well as to the aneuploidy.

Figure 7:
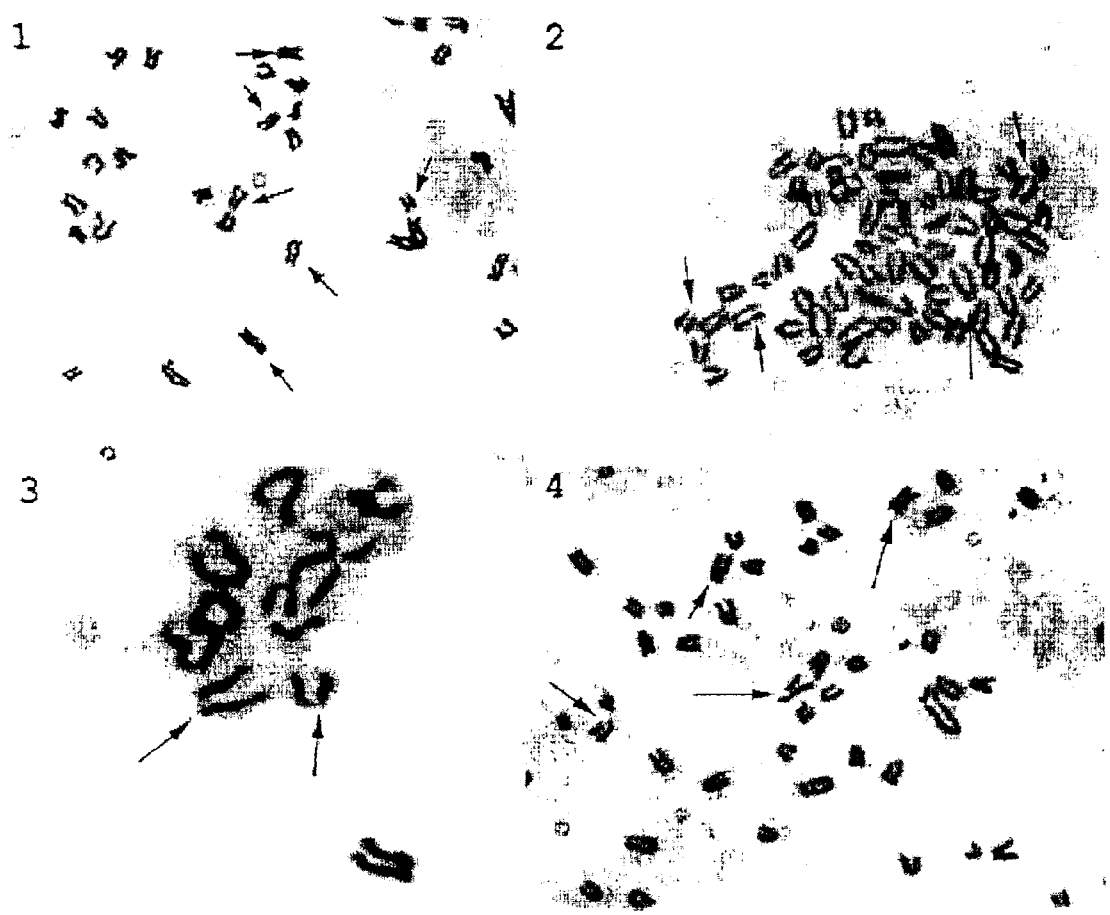
FIG. 7 illustrates premature centromere division in PTTG −/− MEFs. Four different fields are depicted, the centromere region showing premature division are arrowed in each field, with a magnification of 400×. The chromosomal spreads were obtained using standard cytogenetic procedures. (*The AGT cytogenetics laboratory manual*, 3rd ed., Lippincott-Raven Publishers, Philadelphia [1997]).

Notably, premature centromere division, whose genetic mechanism is unclear, was also observed in ~10% of PTTG -/- MEFs (FIG. 7). Premature centromere division is defined as separation of the centromere region preceding completion of chromosome arm separation. Normally, the centromere region is the last region to separate. In the 5 out of 54 chromosome spreads of PTTG -/- MEFs with premature centromere division, 2–5 chromosomes were affected in each cell. No such premature centromere division was observed in PTTG +/+ MEFs. However, the presence of these aberrant chromosome structures in the PTTG -/- MEFs was not lethal for the entire cell population.

EXAMPLE 7

Testicular, Thymic and Splenic Size Study with PTTG Null Mutant Rodents and Thymic Lymphocytes Method PTTG +/+ and -/- mice were sacrificed and their respective spleen weights and thymus sized were measured.

Results

PTTG -/- mice had reduced testicle weight, reduced spleen weights and enlarged thymus (Table 3, FIG. 4A) while ovarian weights did not differ. Testicular hypoplasia was more severe in sexually mature than in immature mice (Table 3). The PTTG -/- adult testicle weight was 45–55% of PTTG +/+ mice. Splenic hypoplasia was apparent after weaning and continues for up to 8 months observation time, with PTTG -/- spleen weight being 50–75% of PTTG +/+ mice. Thymic hyperplasia was more pronounced at an early age (4–5 weeks). PTTG is abundantly expressed in normal testis and thymus, but not in spleen or ovary. (Wang, Z. Melmed, S., *Characterization of the Murine pituitary tumor transforming gene (PTTG) and its promoter*, Endocrinology 141:763–771 [2000].) The weight changes observed in testis and thymus thus suggest cell type differences in PTTG effects cell growth. Thymic hyperplasia is probably not due to reduced apoptosis, as PTTG -/- thymocytes demonstrated similar in vitro responses to 20 nM dexamethasone or 3 Gy irradiation as compared to WT thymocytes (data not shown), and similar to GADD45a -/- mice with thymic hyperplasia despite functioning thymocyte apoptosis mechanisms. (Hollander, M. C., et al., *Genomic instability in Gadd45a-deficient mice*, Nature Genetics, 23:176–184 [1999]).

TABLE 3

Phenotype Comparison Between PTTG +/+ and PTTG −/− mice

| Phenotype | Sex, age | PTTG +/+ | PTGG −/− |
|---|---|---|---|
| Testis weight (mg) | male, 4 weeks | 26.2 ± 2.3 | 22.1 ± 1.7 |
| | male, 30 weeks | 108.3 ± 10.1 | 50.6 ± 5.2 |
| Spleen weight (mg) | male, 4–5 weeks | 65.4 ± 5.7 | 36.5 ± 3.2 |
| | male, 30–32 weeks | 101.6 ± 9.6 | 81.1 ± 7.5 |
| | female, 4–5 weeks | 60.8 ± 5.1 | 34.2 ± 3.0 |
| | female, 30–32 weeks | 94.3 ± 8.8 | 81.6 ± 7.7 |
| Thymus weight (mg) | male, 4–5 weeks | 48.4 ± 4.2 | 66.1 ± 5.9 |
| | male, 30–32 weeks | 32.9 ± 2.8 | 38.3 ± 2.9 |
| | female, 4–5 weeks | 60.5 ± 5.5 | 82.2 ± 6.3 |
| | female, 30–32 weeks | 44.7 ± 4.0 | 52.4 ± 4.5 |
| Platelets (1,000/ul) | male, 4–5 weeks | 1,020 ± 93 | 680 ± 45 |
| | female, 4–5 weeks | 850 ± 61 | 370 ± 28 |
| | female, 7–9 weeks | 1,080 ± 97 | 660 ± 52 |

Note:
All values are mean ± SD (n = 5–6 per group)

EXAMPLE 8

CD4 and CD8 Surface Expression in Thymic Lymphocytes

Thymic lymphocytes were isolated from PTTG +/+ and PTTG −/− mice aged 5–6 weeks and cultured in RPMI 1640 medium. Isolated thymocytes were also stained for CD4 and CD8 surface expression using PE labeled anti-CD4 (L3T4) and FITC labeled anti-CD8 (Ly-2) (BD PharMingen) and analyzed using FACS-Star (Becton Dickinson).

The distribution of CD4+CD8+, CD4+CD8− and CD4−CD8+ thymocytes significantly differed after PTTG disruption (FIG. 4B): CD4+CD8− thymocytes represent ~13.5% of total PTTG −/− thymocytes vs. ~6.5% in PTTG +/+ mice.

---

We claim:

1. A null mutant mouse comprising in its germ cells an artificially induced pituitary tumor transforming gene (PTTG) null mutation on both PTTG alleles, wherein said mutation results in said mouse exhibiting at least one phenotype selected from the group consisting of hyperglycemia, hypoinsulinaemia, hypoleptinemia, diabetes, chromosomal aneuploidy, premature centromere division, chromosomal damage, aberrant mitotic cellular division, thrombocytopenia, thymic hyperplasia, splenic hypoplasia, testicular hypoplasia, and female subfertility, the prevalence of which is greater than in a mouse lacking said mutation.

2. The null mutant mouse of claim 1, wherein functional PTTG protein is not expressed in the somatic cells of said mouse.

3. The null mutant mouse of claim 1, wherein the cells of said mouse lack the ability to endogenously express functional PTTG protein.

4. The null mutant mouse of claim 1, wherein both PTTG genes have been artificially mutated by way of homologous recombination.

5. The null mutant mouse of claim 1, wherein the PTTG null mutant was generated by a mating of a male mouse and female mouse each bearing at least one artificially mutated PTTG allele.

6. The null mutant mouse of claim 5, wherein said at least one mutated PTTG allele is generated by way of homologous recombination.

7. The null mutant mouse of claim 5, wherein said at least one mutated PTTG allele is generated by way of homologous recombination in an embryonic stem cell.

8. The null mutant mouse of claim 7, wherein the embryonic stem cell is from the stem cell line murine ES J-1.

9. The null mutant mouse of claim 7, wherein said embryonic stem cell is injected into a blastocyst, and wherein the blastocyst is implanted into a pseudopregnant mouse.

10. The null mutant mouse of claim 5, wherein said at least one mutated PTTG allele is generated by way of homologous recombination in an embryonic stein cell, and wherein at least one mouse genomic copy of the PTTG gene in the embryonic stem cell recombines with a targeting vector containing a selectable genetic marker sequence, such that said targeting vector is inserted into the genome of said embryonic stem cell.

11. The null mutant mouse of claim 5, wherein said at least one mutated PTTG allele contains a deletion of the translation start site, the KOZAK region, a segment of the endogenous PTTG gene promoter region, the transcription start codon, or any combination thereof.

12. The null mutant mouse of claim 5, wherein said at least one mutated PTTG allele is generated by way of site specific recombination, transportational recombination, a frame shift mutation, homologous recombination in a germ cell, or any combination thereof.

13. The null mutant mouse of claim 12, wherein the germ cell is an oocyte or a male germ cell.

14. A mouse whose germ line comprises an artificially induced pituitary tumor transforming gene (PTTG) null mutation on both PTTG alleles, wherein said mutation results in said mouse exhibiting at least one phenotype selected from the group consisting of hyperglycemia, hypoinsulinaemia, hypoleptinemia, diabetes, chromosomal aneuploidy, premature centromere division, chromosomal damage, aberrant mitotic cellular division, thrombocytopenia, thymic hyperplasia, splenic hypoplasia, testicular hypoplasia, and female subfertility, the prevalence of which is greater than in a mouse lacking said mutation, and wherein both mutated PTTG genes are transmitted to said mouse by a mating of a male mouse and female mouse each bearing at least one artificially mutated PTTG allele; said at least one mutated PTTG allele is generated by way of homologous recombination with a targeting vector; and said targeting vector further comprises a selectable genetic marker; said targeting vector contains a polynucleotide sequence comprising a segment of PTTG genomic DNA or a PTTG cDNA spanning the PTTG KOZAK sequence from which the KOZAK sequence has been deleted and replaced with polynucleotides exogenous to the PTTG gene, and said exogenous polynucleotides are flanked by at least about 200 polynucleotide base pairs that are complementary to polynucleotide regions of an endogenous PTTG gene which flank the endogenous KOZAK sequence.

15. A mouse whose germ line comprises an artificially induced pituitary tumor transforming gene (PTTG) null mutation on both PTTG alleles, wherein said mutation results in said mouse exhibiting at least one phenotype selected from the group consisting of hyperglycemia, hypoinsulinaemia, hypoleptinemia, diabetes, chromosomal aneuploidy, premature centromere division, chromosomal damage, aberrant mitotic cellular division, thrombocytopenia, thymic hyperplasia, splenic hypoplasia, testicular hypoplasia, and female subfertility, the prevalence of which is greater than in a mouse lacking said mutation, and wherein both mutated PTTG genes are transmitted to said mouse by a mating of a male mouse and female mouse each bearing at least one artificially mutated PTTG allele; said at least one mutated PTTG allele is generated by way of homologous recombination with a targeting vector; and said targeting vector further comprises a selectable genetic marker; said targeting vector contains a polynucleotide sequence comprising a segment of PTTG genomic DNA or a PTTG cDNA spanning the PTTG translation start site from which the translation start site has been deleted and replaced with polynucleotides exogenous to the PTTG gene; and said exogenous polynucleotides are flanked by at least about 200 polynucleotide base pairs that are complementary to polynucleotide regions of an endogenous PTTG gene which flank the endogenous translation start site.

16. A mouse whose germ line comprises an artificially induced pituitary tumor transforming gene (PTTG) null mutation on both PTTG alleles, wherein said mutation results in said mouse exhibiting at least one phenotype selected from the group consisting of hyperglycemia, hypoinsulinaemia, hypoleptinemia, diabetes, chromosomal aneuploidy, premature centromere division, chromosomal damage, aberrant mitotic cellular division, thrombocytopenia, thymic hyperplasia, splenic hypoplasia, testicular hypoplasia, and female subfertility, the prevalence of which is greater than in a mouse lacking said mutation, and wherein both mutated PTTG genes are transmitted to said mouse by a mating of a male mouse and female mouse each bearing at least one artificially mutated PTTG allele; said at least one mutated PTTG allele is generated by way of homologous recombination with a targeting vector; and said targeting vector further comprises a selectable genetic marker; said targeting vector contains a polynucleotide sequence comprising a segment of PTTG genomic DNA or a PTTG cDNA spanning the PTTG transcription start codon from which the transcription start site has been deleted and replaced with polynucleotides exogenous to the PTTG gene; and said exogenous polynucleotides are flanked by at least about 200 polynucleotide base pairs that are complementary to polynucleotide regions of an endogenous PTTG gene which flank the endogenous transcription start codon.

17. An animal model for diabetes comprising a null mutant mouse comprising in its germ cells an artificially induced pituitary tumor transforming gene (PTTG) null mutation on both PTTG alleles, wherein said mutation results in said mouse exhibiting diabetes, the prevalence of which is greater than in a mouse lacking said mutation.

18. A method for screening a drug candidate for therapeutic treatment of a disease condition selected from the group consisting of diabetes, hyperglycemia, hypoinsulinaemia, and hypoleptinemia, comprising:
    providing a null mutant mouse comprising in its germ cells an artificially induced PTTG null mutation on both PTTG alleles, wherein said mutation results in said mouse exhibiting at least one phenotype selected from the group consisting of hyperglycemia, hypoinsulinaemia, hypoleptinemia, diabetes, chromosomal aneuploidy, premature centromere division, chromosomal damage, aberrant mitotic cellular division, thrombocytopenia, thymic hyperplasia, splenic hypoplasia, testicular hypoplasia, and female subfertility, the prevalence of which is greater than in a mouse lacking said mutation;
    administering said drug candidate to said mouse; and
    determining potential efficiency of said drug candidate for the treatment of said disease condition based on a response of said mouse to said drug candidate.

* * * * *

SEQUENCE LISTING

<160> NUMBER OF SEQ ID NOS: 5

<210> SEQ ID NO 1
<211> LENGTH: 191
<212> TYPE: DNA
<213> ORGANISM: Mus musculus

<400> SEQUENCE: 1
caccagtcac acatcagcat ctcctgtggc tccatagagc tgaggacttt acaagctgtc     60
acaacctttg tagaaagggt ctgtccagca ggaggggtg gggtggggtg ggtgaaattc    120
ctagtacaag tatcccagta tcaatcatgg aactttagaa tgttttcagg aacacacaaa    180
ggagactaag g                                                         191

<210> SEQ ID NO 2
<211> LENGTH: 20
<212> TYPE: DNA
<213> ORGANISM: Mus musculus

<400> SEQUENCE: 2
ggtttcaacg ccacgagtcg                                                 20

<210> SEQ ID NO 3
<211> LENGTH: 25
<212> TYPE: DNA
<213> ORGANISM: Mus musculus

<400> SEQUENCE: 3
ctggcttttc agtaacgctg ttgac                                           25

<210> SEQ ID NO 4
<211> LENGTH: 24
<212> TYPE: DNA
<213> ORGANISM: Mus musculus

<400> SEQUENCE: 4
gtgctacttc catttgtcac gtcc                                            24

```
<210> SEQ ID NO 5
<211> LENGTH: 24
<212> TYPE: DNA
<213> ORGANISM: Mus musculus

<400> SEQUENCE: 5
gtgctacttc catttgtcac gtcc                                              24
```